(12) United States Patent
Bertrand et al.

(10) Patent No.: US 10,345,320 B2
(45) Date of Patent: *Jul. 9, 2019

(54) SYSTEMS AND METHODS FOR PERFORMING AMPLICON RESCUE MULTIPLEX POLYMERASE CHAIN REACTION (PCR)

(71) Applicant: iCubate, Inc., Huntsville, AL (US)

(72) Inventors: Jeff Bertrand, Hazel Green, AL (US); Jian Han, Huntsville, AL (US); Phillip Ewing, Madison, AL (US)

(73) Assignee: iCubate, Inc., Huntsville, AL (US)

( * ) Notice: Subject to any disclaimer, the term of this patent is extended or adjusted under 35 U.S.C. 154(b) by 613 days.

This patent is subject to a terminal disclaimer.

(21) Appl. No.: 14/552,181

(22) Filed: Nov. 24, 2014

(65) Prior Publication Data
US 2015/0080259 A1 Mar. 19, 2015

Related U.S. Application Data

(63) Continuation of application No. 13/674,858, filed on Nov. 12, 2012, now Pat. No. 8,911,949.
(Continued)

(51) Int. Cl.
*C12Q 1/68* (2018.01)
*G01N 35/00* (2006.01)
(Continued)

(52) U.S. Cl.
CPC ........ *G01N 35/00029* (2013.01); *B01L 3/502* (2013.01); *B01L 7/52* (2013.01);
(Continued)

(58) Field of Classification Search
None
See application file for complete search history.

(56) References Cited

U.S. PATENT DOCUMENTS

| | | |
|---|---|---|
| 5,658,531 A | 8/1997 | Cope et al. |
| 5,955,736 A | 9/1999 | Robinson et al. |
| 7,331,483 B2 | 2/2008 | Bhimani et al. |
| 7,999,092 B2 | 8/2011 | Han |
| 8,333,937 B2 | 12/2012 | Hanafusa et al. |
| 8,383,068 B2 | 2/2013 | Bertrand et al. |

(Continued)

FOREIGN PATENT DOCUMENTS

| | | |
|---|---|---|
| EP | 0246632 | 5/1987 |
| EP | 1941948 | 12/2006 |

*Primary Examiner* — Kaijiang Zhang
(74) *Attorney, Agent, or Firm* — Maynard Cooper & Gale, P.C.; Jon E. Holland

(57) ABSTRACT

Embodiments of the present disclosure generally pertain to systems and methods for performing amplicon rescue multiplex polymerase chain reaction (arm-PCR). In one embodiment, the system comprises a processor and a reader coupled to a control element. The control element is configured to control the operation of the processor and the reader based on a variety of settings. The processor is configured to receive a self-contained cassette for performing PCR amplification of DNA and/or RNA obtained from an organic specimen. The processor engages with the cassette and manipulates reagents within the cassette in order to amplify and detect the DNA from the specimen. The processor also causes the cassette to deposit the DNA on a microarray within the cassette. The reader is configured to receive the cassette after it has been processed by the processor and to capture an image of the microarray for transmission to the control element as test data. The control element is further configured to analyze the test data received from the reader and to produce an output indicative of a comparison of the test data to predefined data.

12 Claims, 25 Drawing Sheets

Related U.S. Application Data

(60) Provisional application No. 61/558,791, filed on Nov. 11, 2011, provisional application No. 61/592,372, filed on Jan. 30, 2012.

(51) Int. Cl.

| | | |
|---|---|---|
| *B01L 7/00* | (2006.01) | |
| *C12Q 1/6848* | (2018.01) | |
| *B01L 3/00* | (2006.01) | |
| *C12Q 1/686* | (2018.01) | |
| *G01N 35/10* | (2006.01) | |
| *B01L 3/02* | (2006.01) | |

(52) U.S. Cl.
CPC .......... *C12Q 1/686* (2013.01); *C12Q 1/6848* (2013.01); *G01N 35/10* (2013.01); *G01N 35/1011* (2013.01); *G01N 35/1081* (2013.01); *B01L 3/021* (2013.01); *B01L 2200/10* (2013.01); *B01L 2400/0487* (2013.01); *B01L 2400/0644* (2013.01); *G01N 2035/00158* (2013.01); *G01N 2035/00366* (2013.01); *G01N 2035/00801* (2013.01); *G01N 2035/00851* (2013.01)

(56) References Cited

U.S. PATENT DOCUMENTS

| | | |
|---|---|---|
| 8,911,949 B2 | 12/2014 | Bertrand et al. |
| 2002/0142454 A1 | 10/2002 | Cracauer et al. |
| 2004/0208795 A1 | 10/2004 | Hiroatsu et al. |
| 2004/0262162 A1 | 12/2004 | Roach et al. |
| 2005/0089444 A1 | 4/2005 | Justin et al. |
| 2005/0158787 A1 | 7/2005 | Hongo et al. |
| 2007/0264655 A1 | 11/2007 | Netsu |
| 2007/0292941 A1 | 12/2007 | Handique et al. |
| 2008/0038813 A1 | 2/2008 | Chen |
| 2008/0085521 A1 | 4/2008 | Knapp et al. |
| 2009/0280572 A1 | 11/2009 | Ribeiro et al. |
| 2010/0028986 A1 | 2/2010 | Hanafusa |
| 2010/0173394 A1 | 7/2010 | Colston et al. |
| 2011/0076735 A1 | 3/2011 | Jovanovich et al. |

SYSTEMS AND METHODS FOR PERFORMING AMPLICON RESCUE MULTIPLEX POLYMERASE CHAIN REACTION (PCR)

CROSS REFERENCE TO RELATED APPLICATIONS

This application is a continuation of and claims priority to U.S. patent application Ser. No. 13/674,858, entitled "Systems and Methods for Performing Amplicon Rescue Multiplex Polymerase Chain reaction (PCR)" and filed on Nov. 12, 2012, which is incorporated herein by reference. U.S. patent application Ser. No. 13/674,858 claims priority to U.S. Provisional Patent Application No. 61/558,791, entitled "Systems and Methods for Performing Amplicon Rescue Multiplex Polymerase Chain Reaction" and filed on Nov. 11, 2011, which is incorporated herein by reference. U.S. patent application Ser. No. 13/674,858 also claims priority to U.S. Provisional Patent Application No. 61/592,372, entitled "Systems and Methods for Performing Amplicon Rescue Multiplex Polymerase Chain Reaction (PCR)," and filed on Jan. 30, 2012, which is incorporated herein by reference.

RELATED ART

The development of the polymerase chain reaction (PCR) enables the use of DNA amplification for a variety of uses, including molecular diagnostic testing. However, there are challenges associated with the use of PCR for molecular differential diagnostic (MDD) assays. PCR utilizes specific primers or primer sets, temperature conditions, and enzymes. PCR reactions may easily be contaminated, primer binding may require different conditions for different primers, primers should be specific for a target sequence in order to amplify only that target sequence, etc. This has made it even more difficult to amplify multiple sequences from a single sample.

Diagnostic testing of clinical samples to find one or more causative disease agents has, in the past, required that microorganisms be isolated and cultured. However, this may take days while in many cases a diagnosis must be acted upon within hours if the patient's life is to be saved. Identification of one or more disease-causing agents within a clinical sample within a matter of hours is the goal, and methods have been developed to better accomplish that goal. For example, multiplex PCR and target-enriched multiplex PCR (tem-PCR) techniques have been developed to amplify multiple nucleic acids within a sample in order to produce enough DNA/RNA to enable detection and identification of multiple organisms. Mutliplex and tem-PCR techniques offer the ability to perform multiple assays at a time on a single sample, but they must do so by sacrificing much of the sensitivity that can be achieved by single amplification reactions using a single set of target-specific primers. It is still desirable to improve upon the technology in order to provide diagnostic tests with greater sensitivity and shorter diagnostic time. It is also desirable to integrate the amplification and detection steps so that open-tube hybridization steps can be eliminated to reduce false positives caused by carry-over contamination by PCR products.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 27B is a side view of the balancing weight comprising two pinion gears.

FIG. 27C is a side view of the balancing weight comprising one pinion gear.

DETAILED DESCRIPTION

Embodiments of the present disclosure generally pertain to systems and methods for performing amplicon rescue multiplex polymerase chain reaction (arm-PCR). In one embodiment, the system comprises a processor and a reader coupled to a control element. The control element is configured to control the operation of the processor and the reader based on a variety of settings. The processor is configured to receive a self-contained cassette for performing PCR amplification of DNA and/or RNA obtained from an organic specimen. The processor engages with the cassette and manipulates reagents within the cassette in order to amplify and detect the DNA from the specimen. The processor also causes the cassette to deposit the DNA on a microarray within the cassette. The reader is configured to receive the cassette after it has been processed by the processor and to capture an image of the microarray for transmission to the control element as test data. The control element is further configured to analyze the test data received from the reader and to produce an output indicative of a comparison of the test data to predefined data.

Figure 1:
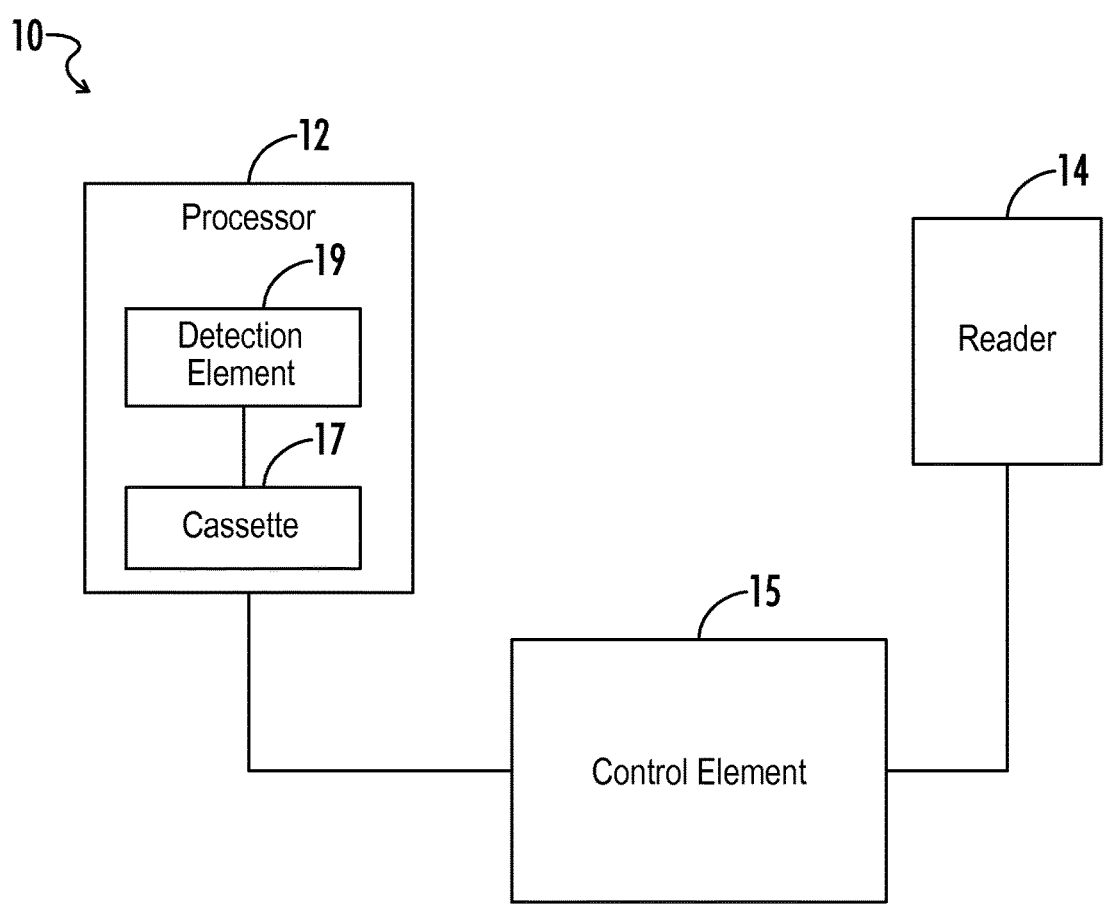
FIG. 1 is a block diagram illustrating an exemplary system for performing PCR amplification in accordance with the present disclosure.

FIG. 1 depicts an exemplary system 10 for performing PCR amplification of DNA and/or RNA obtained from an organic specimen. The system 10 enables the performance of arm-PCR, a technique that has been described previously in U.S. Pat. No. 7,999,092, entitled "Amplicon Rescue Multiplex Polymerase Chain Reaction for Amplication of Multiple Targets," which is incorporated herein by reference. The system 10 comprises a processor 12 and a reader 14 coupled to a control element 15. In one embodiment, the control element 15 comprises a computing device, such as, for example, a computer, although other types of control elements 15 are possible in other embodiments. The control element 15 is configured to communicate with the processor 12 and the reader 14 in order to control the operation of the processor 12 and the reader 14 based on a variety of settings, discussed in more detail hereafter. The control element 15 is further configured to receive data indicative of the specimen's amplified DNA from the reader 14 and to produce an output indicating a comparison of the amplified DNA to predefined data, discussed in more detail hereafter. Such comparison is used in diagnosing the specimen.

The processor 12 is configured to receive a self-contained cassette 17 containing the organic specimen, to engage with the cassette 17, and to manipulate the cassette 17 such that arm-PCR is performed on the specimen within the cassette 17. An exemplary cassette is disclosed in U.S. Pat. No. 8,383,068, entitled "Apparatus for Performing Amplicon Rescue Multiplex PCR," which is incorporated herein by reference. In one embodiment, the processor 12 comprises at least one detection element 19 for detecting the cassette 17 within the processor 12 and determining a variety of information about the cassette 17. The detection element 19 transmits the information to the control element 15, and the control element 15 manipulates the processor 12 based on the information, as will be discussed in more detail hereafter.

The reader 14 is configured to receive the cassette 17 after the cassette 17 has been processed by the processor 12 and to capture an image of a microarray (not shown) on the cassette 17. The microarray indicates detection of the DNA, which is produced by PCR amplification. In one embodiment, the image of the microarray comprises a digital image, although other types of images are possible in other embodiments. The reader 14 is further configured to transmit the image to the control element 15 as test data in order to allow the control element 15 to analyze the test data and compare the test data to the predefined data.

Figure 2:
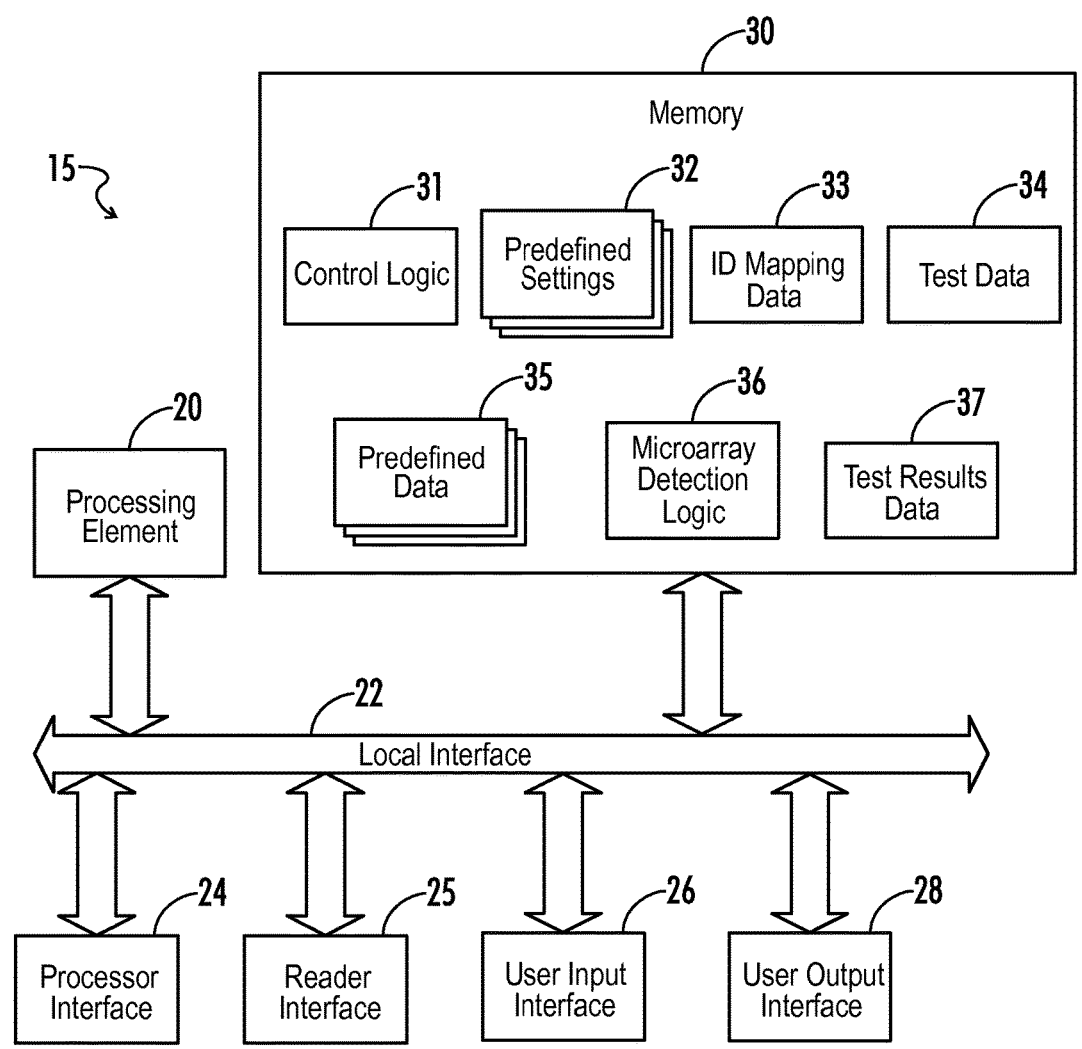
FIG. 2 is a block diagram illustrating an exemplary embodiment of a control element, such as is depicted by FIG. 1.

FIG. 2 depicts an exemplary embodiment of the control element 15 of FIG. 1. As set forth above, the control element 15 is coupled to at least one processor 12 (FIG. 1) and at least one reader 14 (FIG. 1) of the system 10, and the control element 15 is configured to communicate with, monitor, and control the operation of the processor 12 and the reader 14. The control element 15 is further configured to receive test data from the reader 14 and to analyze the test data, as will be discussed in more detail hereafter. In one embodiment, the control element 15 is implemented via a computer, such as a desktop or laptop computer, but other types of devices may be used to implement the control element 15 in other embodiments.

As shown by FIG. 2, the control element 15 comprises at least one conventional processing element 20, such as a digital signal processor (DSP) or a central processing unit (CPU), that communicates to and drives the other elements within the control element 15 via a local interface 22, which can include at least one bus. The control element 15 further comprises a processor interface 24 for enabling communication with the processor 12 and a reader interface 25 for enabling communication with the reader 14. In one embodiment, the processor interface 24 receives status information from the processor 12 and allows the control element 15 to control the operation of the processor 12 based on a plurality of settings, discussed in more detail hereafter. In one embodiment, the reader interface 25 receives status information from the reader 14 and allows the control element 15 to control the operation of the reader 14. Furthermore, the reader interface 25 receives data from the reader 14 in the form of an image of the microarray indicative of the amplified DNA from the specimen. The control element 15 further comprises a user input interface 26, such as, for example, a computer keyboard and/or mouse, and a user output interface 28, such as, for example, a computer monitor and/or printer. However, different user input and output interfaces 26 and 28 are possible in other embodiments.

The control element 15 further comprises control logic 31 configured to control the operation of the processor 12 and the reader 14 and to manage data and other components within the control element 15. In this regard, in one embodiment, the control logic 31 manages application of an appropriate set of predefined settings 32 and an appropriate set of predefined data 35 for the cassette 17 by mapping the cassette 17 to the appropriate set of the settings 32 and the data 35 based on ID mapping data 33 and/or information input by a user via the user input interface 26. The ID mapping data 33 is stored in memory 30 of the control element 15 and maps an identifier (not shown) on and associated with the cassette 17 (e.g., a bar code), as detected by the detection element 19 (FIG. 1), to a corresponding set of predefined settings 32 and a set of predefined data 35 for that cassette 17. Each set of predefined settings 32 is stored in memory 30 of the control element 15 and indicates a variety of operations to be executed by the processor 12 in order to perform arm-PCR for a corresponding cassette 17. Each set of predefined data 35 indicates a set (e.g., one or more) of dots of the cassette's microarray that will fluoresce during reading due to DNA from a target agent gathered at the dot, as will be discussed in more detail hereafter. The predefined data 35 is compared to test data 34 indicating the dots of the microarray that have fluoresced during reading in order to determine whether the target agent is present in the specimen. The predefined settings 32 may vary depending on the type of tests being run on the specimen (e.g., the type of target agent the test is designed to detect in the specimen). For example, a set of the predefined settings 32 may indicate information such as the length of time heaters (not shown in FIG. 2) are applied to the cassette 17 to perform arm-PCR for a target agent, the temperatures of the respective heaters, and the order of specific operations to be performed by the processor 12 in order to effectively manipulate the cassette 17 to perform arm-PCR for the target agent, discussed in more detail hereafter.

In one embodiment, the predefined settings 32 include a plurality of sets of operations to be performed by the processor 12. In one exemplary embodiment, the predefined settings 32 include three sets of settings. In such embodiment, the three sets of settings 32 are tailored for high specificity, high sensitivity, and nominal results. In this regard, if the set of the settings 32 tailored for high specificity is chosen, the processor 12 performs operations on the cassette 17 aimed at isolating a specific target agent or DNA sequence in a specimen and excluding all other target agents or DNA sequences. However, if the set of settings, tailored for high sensitivity is chosen, the processor 12 performs operations on the cassette 17 aimed at identifying a broad range of target agents or DNA sequences in a specimen. Furthermore, if the nominal set of settings is chosen, the processor 12 performs operations on the cassette 17 aimed at producing a nominal range of target agents or DNA sequences. However, there may be a different numbers and types of sets of settings in other embodiments.

In one embodiment, the sets of the predefined settings 32 may be used for a closed platform and an open platform. In this regard, the closed platform allows specific tests to be performed for particular target agents, such as, for example, Food and Drug Administration (FDA)-regulated target agents, while the open platform allows a wide variety of tests to be performed for unregulated target agents. For example, a set of the predefined settings 32 for the closed platform may be automatically selected by the control logic 31 based on the target agent as indicated by the ID mapping data 33. Thus, the user may not select or otherwise control the test performed on the target agent on the closed platform. However, for the open platform, the user may manually select a desired set of the predefined settings 32 via the user input interface 26 in order to obtain a desired result. In the exemplary embodiment set forth above, the user may select one of three sets of the predefined settings 32 to be performed on the cassette 17 wherein the sets are tailored for high specificity, high sensitivity, or nominal results. However, different types and numbers of sets of the predefined settings 32 may be selected by the user on the open platform in other embodiments. Furthermore, in one embodiment, the user may define a custom set of settings to be performed on the cassette 17 on the open platform. Thus, on the open platform, the user may manipulate the tests performed on the target agent by selecting different sets of the settings 32 and varying primers that are used in the tests, as will be discussed in more detail hereafter.

In an embodiment described above, an identifier for the cassette 17 is read by a detection element 19. In other embodiments, other techniques for determining the identifier are possible. As an example, the identifier may be electronically stored in the cassette 17. The cassette 17 may be configured to transmit the identifier wirelessly or otherwise to the detection element 19. As an example, radio frequency (RF) or infrared communication may be used to communicate the identifier. In other embodiments, yet other techniques may be used by the detection element 19 to determine the cassette's identifier.

The control logic 31 is further configured to receive images of the microarray from the reader 14 via the reader interface 25 and to store the images in the memory 30 of the control element 15 as test data 34. In one embodiment, the test data 34 comprises one or more digital images of the microarray for one or more cassettes 17, although different types of test data 34 are possible in other embodiments. The control logic 31 is further configured to compare the test data 34 to the predefined data 35 mapped to the cassette 17 in order to determine whether particular target agents are detected in the specimen. In this regard, in one embodiment, the test data 34 comprises an image of the microarray wherein DNA corresponding to a particular target agent is gathered at a specific dot or combination of dots (not shown) in the microarray. The dot or combination of dots at which the DNA is gathered fluoresce when illuminated with laser light from the reader 14. The reader 14 captures a digital image of the microarray while the microarray is illuminated by a laser, and microarray detection logic 36 is configured to analyze the image to determine which dots fluoresce due to the presence of DNA on or in the dot. As described in more detail herein, each dot is composed of a different material, and the dots are arranged in a predefined pattern. Thus, the pattern of fluorescing dots in the image indicates whether the target agent is present in the sample under test. Moreover, the logic 36 digitally analyzes the image to determine which dots are fluorescing in the image and compares the determined fluorescing pattern to the appropriate set of predefined data 35 for a particular target agent. Based on such comparison, the logic 36 determines whether the target agent is present in the sample under test.

Figure 23:
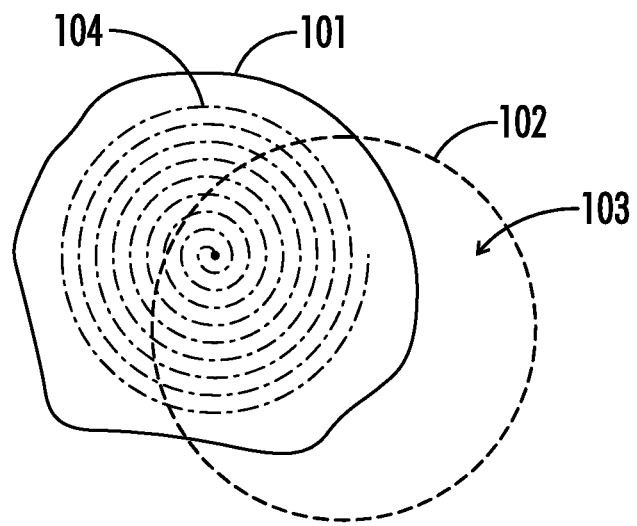
FIG. 23 depicts a portion of a microarray image showing an exemplary dot.

In analyzing the microarray image the logic 36 locates and identifies each dot within the image. There are various techniques that can be used to locate and identify dots. In one exemplary embodiment, the logic 36 identifies area within the digital image, referred to herein as "test areas." Each test area is an area of the digital image in which a particular dot is expected to be located based on the predefined pattern of dots on the microarray. As an example, FIG. 23 depicts a portion of a microarray image showing an exemplary dot 101. The reference line 102, which is not actually visible in the image, represents a test area 103 in which the logic 36 expects to find a dot 101 based on the pixel locations of the test area 103 within the digital image. To determine whether the dot 101 associated with the test area 103 is fluorescing in the image, the logic 36 averages the brightness of all of the pixels within the test area 103 and compares the averaged brightness to a threshold. If the average brightness exceeds the threshold, then the logic 36 determines that the dot 101 is fluorescing in the image. However, if the average brightness does not exceed the threshold, then the logic 36 determines that the dot 101 is not fluorescing in the image.

As shown by FIG. 23, the dot 101 may be slightly misaligned with the test area 103 for a variety of reasons, including imperfections in depositing the material of the dot 101 on the microarray. Such misalignment could result in a false fluorescent determination if a significant portion of the test area 103 is not aligned with the dot 101. Thus, in an effort to improve the test results, the logic 36 automatically moves the image of the dot 101 relative to the test area 103 so that a greater percentage of the dot 101 is within the test area 103. In this regard, before assessing whether the associated dot 101 is fluorescing, as described above, the logic 36 performs an alignment algorithm to reposition the dot 101 within the microarray image.

According to such algorithm, the logic 36 identifies the dot 101 by comparing the pixel color values. In this regard, a group of contiguous pixels having substantially similar color values generally indicate the location of the dot 101 within the image.

Figure 24:
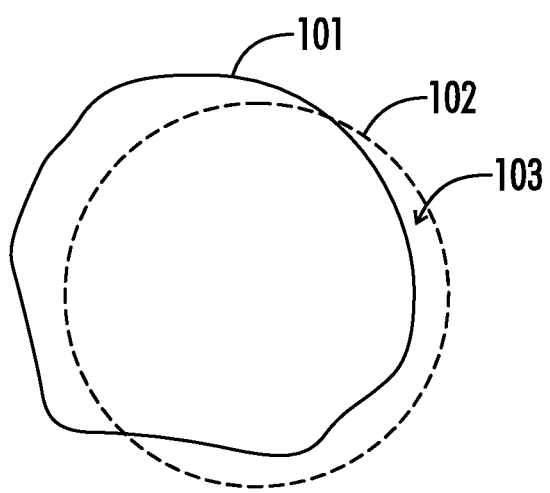
FIG. 24 depicts a portion of a microarray image showing a repositioned exemplary dot.

After identifying the dot 101, the logic 36 is configured to measure the average brightness of the test area 103 associated with the dot 101 (e.g., closest to the dot 101 within the image). The logic 36 then slightly repositions the dot 101 relative to the test area 103 (e.g., moves the dot 101 within the image), as shown by FIG. 24, and again averages the brightness of the pixels within the test area. If the movement causes a greater percentage of the test area 101 to be covered by the dot 101, then the average brightness should increase after the movement. The logic 26 compares the average brightness prior to the movement to the average brightness after the movement, and determines whether the dot 101 is more aligned based on such comparison. In this regard, if the average brightness after the repositioning is higher, then the logic 36 determines that the dot 101 is now more aligned with the test area 101. However, if the average brightness is after repositioning is less, then the logic 36 determines that the dot 101 is now less aligned with the test area 101.

Moreover, the logic 36 continues repositioning the dot 101 and measuring average brightness until a maximum average brightness is found. The position of the dot 101 relative to the test area 103 for such maximum brightness is the position that results in the greatest degree of alignment between the dot 101 and the test area 103. Such position is selected by the logic 103 as the final position within the image to be used for the dot 101.

In one exemplary embodiment, the logic 36 moves the dot 101 in a widening spiral relative to the test area 103 when performing the repositioning algorithm. In this regard, the logic 36 moves the dot 101 such that its center moves along a spiral 104, as shown by FIG. 23. As long as the average brightness of the test area 103 continues to increase for successive number of positions of the dot 101, the logic 36 continues repositioning the dot 101. However, once the average brightness decreases for a successive number of dot positions, the logic 36 stops the repositioning algorithm and selects the position that provided the highest average brightness as the dot's final position within the image. In other embodiments, other techniques and/or movement patterns may be used to find the position for which the dot 101 is most aligned with the test area 103. In one exemplary embodiment, the logic 36 is configured to perform the same repositioning algorithm separately for each dot of the microarray image such that each dot is individually moved to better align it with its respective test area. Once all of the respective dots have been repositioned, the image is stored in memory 30 as test data 34.

The predefined data 35 is stored in memory 30 and indicates for a given cassette 17 one or more dots in the microarray corresponding to a particular target agent. In this regard, the predefined data 35 indicates one or more dots in the microarray that should fluoresce during reading when DNA from a particular target agent is present in the specimen. Thus, if the test data 34 indicates that DNA is detected at one or more particular dots in the microarray, the control logic 31 accesses the predefined data 35 mapped to the cassette 17 to determine which target agent corresponds with the dots. The control logic 31 performs the comparison for each dot in the microarray in order to test for one or more target agents. The control logic 31 transmits results of the comparison between the test data 34 and the predefined data 35 via the user output interface 28. In one embodiment, the control logic 31 stores the test results in the memory 30 as test results data 37 which the user may access via the user output interface 28. For example, for the closed platform, the test results data 37 may indicate a "yes" or "no" for each target agent for which the test is being run in order to indicate whether such target agent is detected in the specimen, but different types of indications are possible. However, for the open platform, the test results data 37 may indicate a value for each dot indicative of the brightness of the dot such that the user may compare various sets of the test results data 37 for a given target agent in order to determine a preferred solution for the target agent, discussed in more detail hereafter.

It should be noted that the control logic 31 and the microarray detection logic 36 can be implemented in software, hardware, firmware or any combination thereof. In an exemplary embodiment illustrated in FIG. 2, the control logic 31 and the microarray detection logic 36 are implemented in software and stored in memory 30 of the control element 15.

Note that the control logic 31 and the microarray detection logic 36, when implemented in software, can be stored and transported on any computer-readable medium for use by or in connection with an instruction execution apparatus that can fetch and execute instructions. In the context of this document, a "computer-readable medium" can be any means that can contain or store a computer program for use by or in connection with an instruction execution apparatus.

Figure 3:
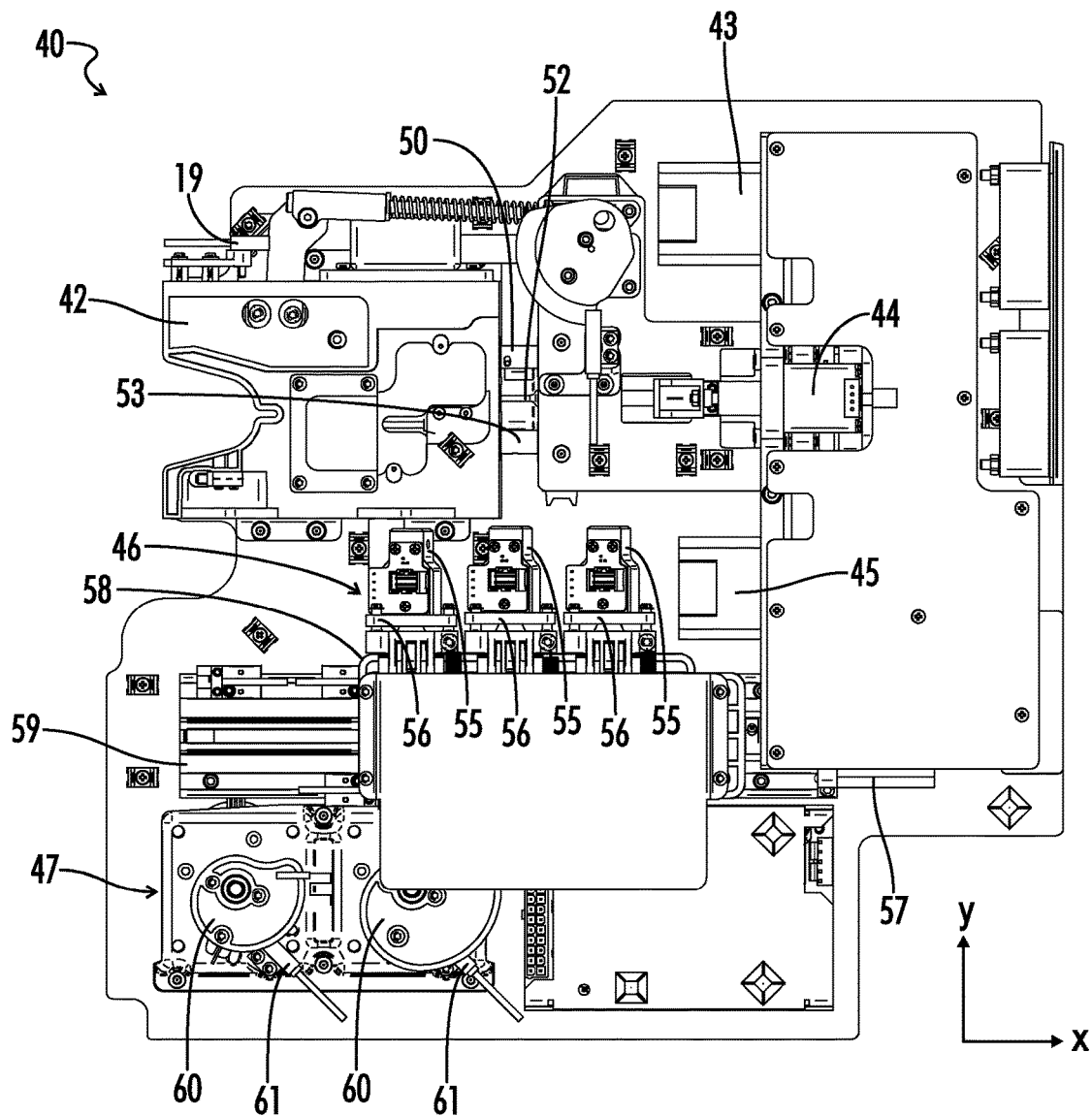
FIG. 3 is a side plan view of an exemplary processor module.

FIG. 3 depicts an exemplary processor module 40 of the processor 12 of FIG. 1. In this regard, the processor 12 comprises one or more processor modules 40. In one embodiment, the processor 12 comprises four processor modules 40 positioned side by side within a housing (not shown), although any number of modules 40 may be utilized in other embodiments. Each processor module 40 is configured to receive and process a single cassette 17 (FIG. 1) such that arm-PCR techniques are performed upon a specimen within the cassette 17. The processor module 40 comprises a receptacle 42 for receiving and housing the cassette 17 while the cassette 17 is located within the module 40. The module 40 further comprises at least one detection element 19 located adjacent to the receptacle 42 for detecting an identifier (not shown) located on an outer surface of the cassette 17 when the cassette 17 is positioned within the receptacle 42. In one embodiment, the detection element 19 comprises a barcode scanner and the identifier comprises a barcode, although other types of detection elements 19 and identifiers may be used in other embodiments. The detection element 19 detects the identifier and transmits the identifier to the control element 15 (FIG. 1) in order to allow the control element 15 to map the identifier to the predefined settings 32 (FIG. 2), as set forth above.

Once the predefined settings 32 are determined, the control element 15 communicates with an onboard control element 48 which controls the operation of the processor module 40 based upon the settings 32. In this regard, the onboard control element 48 controls the operation of a latch motor 41, a cam bar motor 43, a pump pin motor 44, a lead screw motor 45, a heater assembly 46, and a lifter assembly 47. The latch motor 41 controls the operation of a latch (not shown), discussed in more detail hereafter. The cam bar motor 43 is coupled to a cam bar shaft 50 and controls rotation of the cam bar shaft 50, as will be discussed in more detail hereafter. In one embodiment, the cam bar motor 43 is positioned behind the receptacle 42 within the module 40.

The cam bar shaft 50 extends horizontally into a rear opening (not shown) of the receptacle 42 and engages with a cam bar (not shown) of the cassette 17 in order to control clockwise and counterclockwise rotation of the cam bar and manipulate movement of a pipette (not shown) upward and/or downward in a vertical direction within the cassette 17. The pump pin motor 44 is coupled to a plunger 52 and controls lateral movement of the plunger 52, discussed in more detail hereafter. The pump pin motor 44 is positioned behind the receptacle 42 within the module 40, and the plunger 52 extends laterally into the receptacle 42 via an opening (not shown) in the receptacle. The plunger 52 engages with a pump pin (or "push rod") (not shown) of the cassette 17 and operates a pipette pump assembly (not shown) within the cassette 17 such that fluid is either drawn into the pipette or expelled from the pipette due to the plunger 52 compressing the pump pin.

Furthermore, the lead screw motor 45 is rotatably coupled to a lead screw shaft 53 and controls clockwise and counterclockwise rotation of the lead screw shaft 53. In one embodiment, the lead screw motor 45 is positioned behind the receptacle 42 within the module 40, and the lead screw shaft 53 extends horizontally into the receptacle 42. The lead screw shaft 53 engages with the lead screw (not shown) of the cassette 17 in order to control lateral movement of the pipette within the cassette 17. In this regard, rotating the lead screw shaft 53 in a clockwise direction causes the lead screw to rotate in a clockwise direction such that the pipette travels laterally in one direction within the cassette 17, while rotating the lead screw shaft 53 in a counterclockwise direction causes the lead screw to rotate in a counterclockwise direction such that the pipette travels laterally in the opposite direction within the cassette 17. Control of the cam bar, pump pin, and lead screw of the cassette 17 allows the module 40 to manipulate the pipette within the cassette 17 such that the pipette removes fluids from reagent chambers (not shown) or a sample chamber (not shown) within the cassette 17, or injects fluids into a reagent chamber or detection chamber (not shown) within the cassette 17.

The heater assembly 46 comprises a plurality of heaters 55. In one embodiment, the heater assembly 46 comprises three heaters 55, although other numbers of heaters 55 are possible in other embodiments. In one embodiment, the heater assembly 46 is positioned directly below the receptacle 42 within the module 40. Each heater 55 is positioned upon an adjustable base 56 which may move in a vertical direction to adjust the vertical position of the heater 55, as will be described in more detail hereafter. In one embodiment, each heater 55 is set at a particular temperature and remains at that temperature while the module 40 is in operation. For example, in one embodiment, one heater 55 is set at 55 degrees Celsius, one heater 55 is set at 72 degrees Celsius, and one heater 55 is set at 95 degrees Celsius, although different temperatures are possible in other embodiments. However, the temperature of each heater 55 may vary at different times during operation in other embodiments. Each heater 55 has a recess (not shown in FIG. 3) for receiving the sample chamber located in a bottom of the cassette 17. The specimen is inserted into the sample chamber, and the heaters 55 engage with the sample chamber at various times in order to heat the chamber during the performance of arm-PCR on the specimen. Furthermore, in one embodiment, one heater 55 may be raised to contact a microarray (not shown) in a bottom of the detection chamber in order to perform hybridization and extraction.

The heater assembly 46 further comprises a base motor 57, a base plate 58 and a track 59. The base plate 58 is coupled to each of the adjustable bases 56, and the base plate 58 slideably engages with the track 59 in order to facilitate horizontal movement of the heaters 55 along the track 59. In one embodiment, the motor 57 rotatably engages with the base plate 58 in order to facilitate horizontal movement (parallel to the x-direction) of the base plate 58. Thus, when adjustment of the horizontal position of the heaters 55 is desired, the motor 57 causes the base plate 58 to slide horizontally along the track 59 a desired distance.

The module 40 further comprises the lifter assembly 47 positioned beneath the heater assembly 46. The lifter assembly 47 comprises at least one cam 60 and at least one sensor 61. In one embodiment, the assembly 47 comprises two cams 60 and two sensors 61, although other numbers of cams 60 and sensors 61 are possible in other embodiments. Also, the cams 60 are configured to rotate and contact a heater base 56 in order lift the heater 55 into contact with the sample chamber or detection chamber of the cassette 17. In one embodiment, each cam 60 is snail-shaped such that the cam 60 does not contact any of the heater bases 56 when the cam 60 is in a home position, but the cam 60 contacts and lifts the heater base 56 when the cam 60 is in an engaged position. However, different cam shapes are possible in other embodiments. Furthermore, in one embodiment, one cam 60 is configured to lift the heaters 55 to the sample chamber and one cam 60 is configured to lift one heater to the microarray on the detection chamber. However, other configurations are possible in other embodiments. The sensor 61 corresponding to each cam 60 is configured to detect whether the cam 60 is in the home position and to transmit such detection to the onboard control element 48 of item 40.

Figure 4:
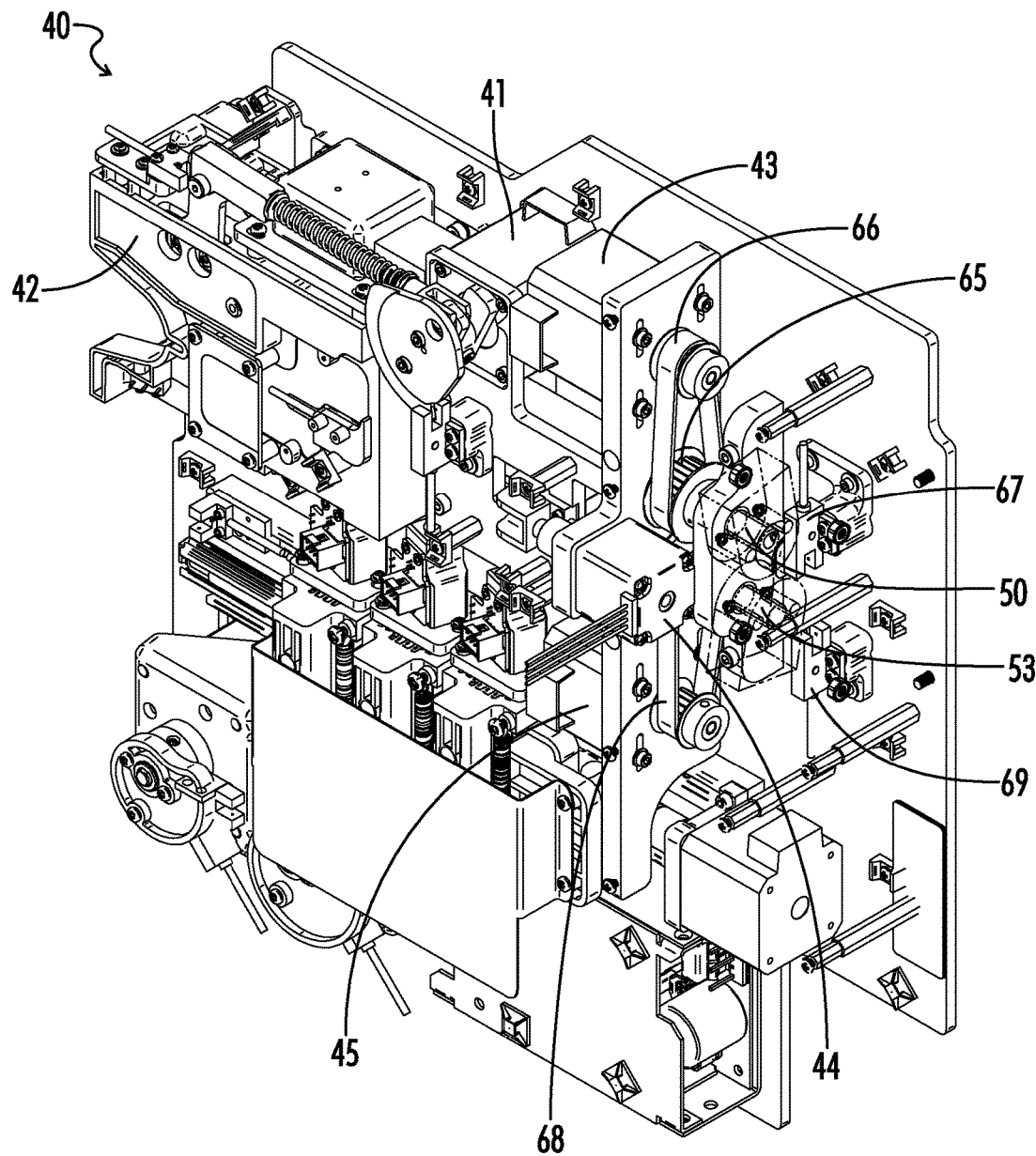
FIG. 4 is a rear perspective view of the processor module of FIG. 3.

FIG. 4 depicts a rear perspective view of the processor module 40 of FIG. 3. As shown in FIG. 4, in one embodiment, the cam bar motor 43 is coupled to a pulley 65 via a belt 66. The pulley 65 is positioned around and coupled to an outer surface of the cam bar shaft 50. The cam bar motor 43 is coupled to the onboard control element 48, which controls the operation of the motor 43 based on the predefined settings 32, as set forth above. When the motor 43 rotates, the belt 66 rotates in the motor's direction of rotation thereby engaging the pulley 65 and causing the cam bar shaft 50 to rotate in the same direction. As set forth above, rotation of the cam bar shaft 50 causes rotation of the cassette's cam bar which adjusts the vertical position of the pipette within the cassette 17. In one embodiment, a cam bar shaft sensor 67 is positioned behind the cam bar shaft 50 and the pulley 65, and the cam bar shaft sensor 67 detects the cam bar shaft 50 when the shaft 50 extends through the sensor 67. The sensor 67 transmits a signal to the control element 48 (FIG. 3) when the cam bar shaft 50 is detected in order to detect insertion of the cassette 17 and maintain the cassette 17 within the receptacle 42 for processing.

The pump pin motor 44 is coupled to the plunger 52 (FIG. 3) and controls the horizontal position of the plunger 52. In one embodiment, the pump pin motor 44 comprises a linear motor, although other types of motors 44 are possible in other embodiments. The motor 44 is coupled to the onboard control element 48, and the control element 48 controls the operation of the motor 44 in order to manipulate the plunger 52 for performing arm-PCR within the cassette 17, as set forth above.

The lead screw motor 45 is coupled to a pulley (not shown in FIG. 4) which is coupled around an outer surface of the lead screw shaft 53. In one embodiment, the lead screw motor 45 is coupled to the pulley via a belt 68. When the motor 45 rotates, the belt 68 rotates in the same direction and engages the pulley such that the pulley and the lead screw shaft 53 pivot in the same direction. Rotation of the lead screw shaft 53 causes the lead screw of the cassette 17 to rotate thereby adjusting the horizontal position of the pipette within the cassette 17 and facilitating arm-PCR. The module 40 further comprises a lead screw shaft sensor 69 positioned behind the lead screw shaft 53 and the pulley. The sensor 69 is configured to detect the shaft 53 and inform the control element 48 of the shaft's position in order to ensure that the shaft 53 has properly engaged with the cassette 17.

Figure 5:
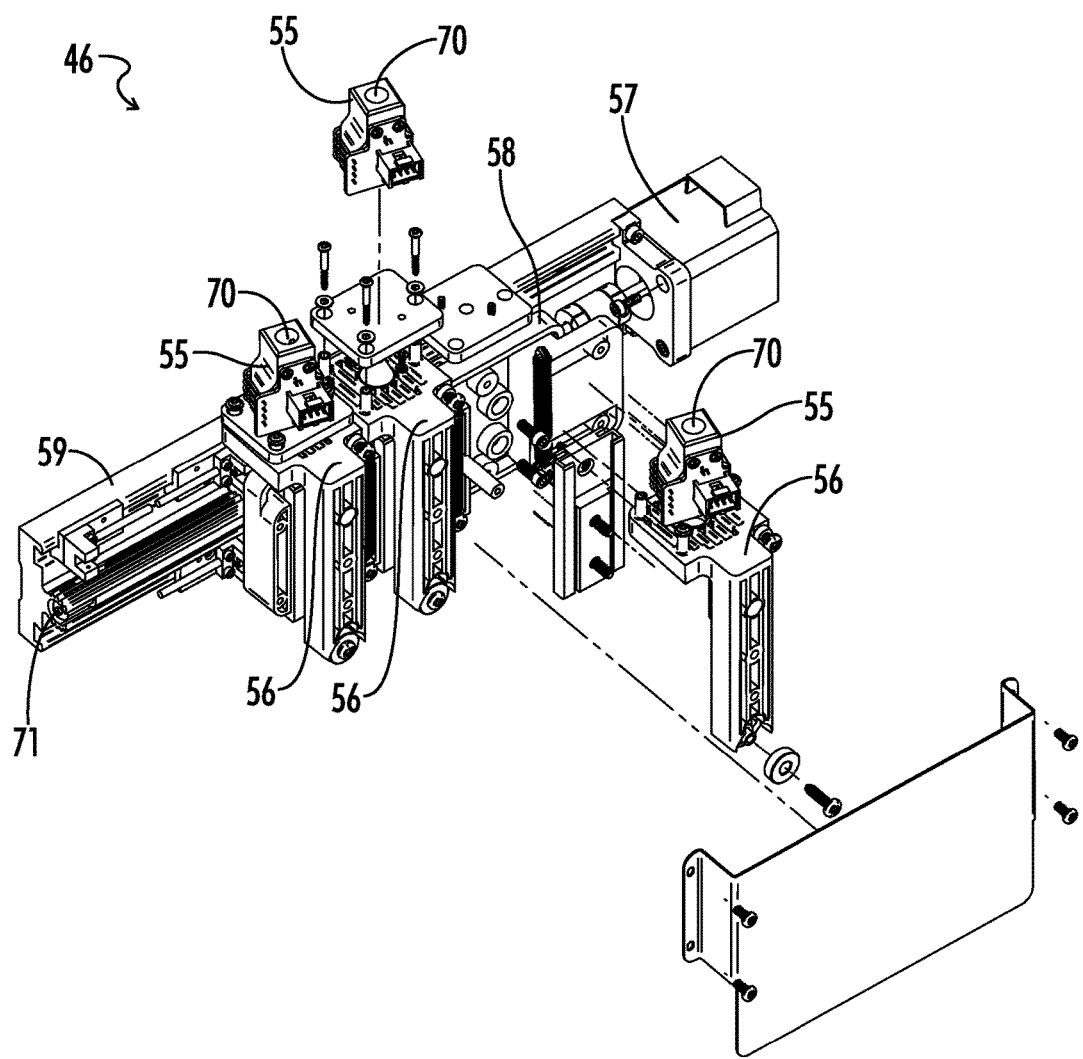
FIG. 5 is a partially exploded view of a heater assembly, such as is depicted by FIG. 3.

FIG. 5 depicts the heater assembly 46 of FIG. 3. The heater assembly 46 comprises the heaters 55, the bases 56, the base motor 57, the base plate 58, and the track 59. In one embodiment, the heater assembly 46 comprises three heaters 55 and three bases 56, although other numbers of heaters 55 and bases 56 are possible in other embodiments. Each heater 55 is positioned upon a base 56, and each base 56 is slideably coupled to the base plate 58. In this regard, each base 56 is coupled to the base plate 58 such that the base 56 may freely move upward and downward (parallel to the y-direction). The cam 60 (FIG. 3), discussed in more detail hereafter, contacts the base 56 and causes the base 56 to slide vertically (parallel to the y-direction) with respect to the base plate 58 in order to bring the heater 55 into contact with the sample chamber or the detection chamber of the cassette 17. Furthermore, each heater 55 has a recess 70 located in a top surface of the heater 55 for receiving the sample chamber of the cassette 17, as will be discussed in more detail hereafter.

The base plate 58 is slideably coupled to the track 59 such that the horizontal position of the base plate 58 may be adjusted. The motor 57 controls the movement of the base plate 58. Thus, when a desired heater 55 is required by the settings 32 to come into contact with the cassette 17, the motor 57 adjusts the horizontal position of the base plate 57 such that the desired heater 55, when raised vertically, will come into contact with the cassette 17. In one embodiment, the base plate 58 engages with the track 59 and has a threaded channel (not shown) for receiving a horizontally-oriented threaded rod 71. The rod 71 is coupled to the motor 57, and rotation of the motor 57 causes rotation of the rod 71 thereby adjusting the horizontal position of the base plate 58 along the track 59. However, other means for adjusting the position of the heaters 55 are possible in other embodiments.

Figure 6:
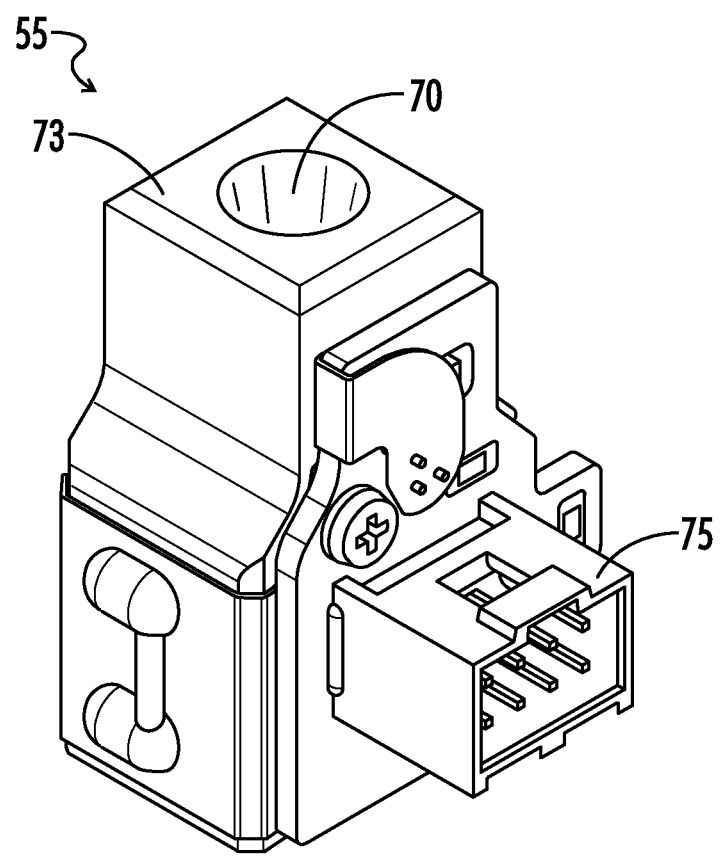
FIG. 6 is a perspective view of an exemplary heater, such as is depicted by FIG. 3.

FIG. 6 depicts an exemplary embodiment of the heater 55 of FIG. 3. In one embodiment, the heater 55 comprises metal, although other materials are possible in other embodiments. The heater 55 has a flat top surface 73 having a concave recess 70 extending down into the surface 73. The recess 70 is dimensioned to receive the sample chamber of the cassette 17 (FIG. 1) such that the chamber fits in the recess 70 and an exterior surface of the chamber contacts the surface defining the recess 70.

In one embodiment, the heater 55 comprises at least one magnet (not shown) positioned in close proximity to the recess 70. In one embodiment, the heater 55 comprises a plurality of electromagnets that may be selectively activated in order to magnetically couple to metallic beads (not shown) within the sample chamber when desired. In this regard, the onboard control element 48 sends a control signal to the heater 55 in order to activate an electromagnet in the heater thereby creating a magnetic flux, which magnetically couples to the beads within the chamber. The beads bond to DNA from the specimen, and the electromagnet magnetically couples to the beads through the sample chamber in order to position the beads in a desirable orientation within the chamber. Magnetically coupling with the beads facilitates steps in the arm-PCR process, such as, for example, addition and/or removal of fluids, without inadvertent removal of the beads from the chamber. As an example, the electromagnets may magnetically couple with the beads in order to hold the beads in the bottom of the sample chamber. The magnets also provide adequate spacing of the beads within the chamber such that all of the DNA attached to the beads is exposed to the arm-PCR process. Other types of magnets, such as, for example, permanent magnets, are possible in other embodiments. When the heater 50 is lifted to the engaged position and receives the sample chamber, the heater 55 transfers heat to the chamber thereby performing steps in the arm-PCR process.

In one exemplary embodiment, an electromagnet close to the bottom of the recess 70 is activated to pull the beads toward the bottom of the sample chamber. To stir or mix the beads, such electromagnet is deactivated, and another electromagnet magnet (e.g., one close to a side of the recess 70) is activated to move the beads from the chamber bottom. The activation states of the electromagnets are then reversed to pull the beads to the bottom of the sample chamber again. However, in other embodiments, the magnets may comprise permanent magnets that are activated and deactivated by raising and lowering the magnets, respectively.

The heater 55 further comprises an electrical interface 75 located on a side of the heater 55. The interface 75 receives power from a power supply (not shown) thereby enabling the heater 55 to reach a desired temperature as set forth in the predefined settings 32 (FIG. 2). In this regard, the heater 55 has internal or external resistive elements (not shown) that generate heat when electrical current is applied thereto. Thus, the control element 48 can control when heat is generated by the heater 55 by controlling an electrical signal that is applied to the resistive elements through the electrical interface 75. The interface 75 also communicates with the control element 48, and the control element 48 communicates with the control element 15 via the processor interface (FIG. 2) and allows the control logic 31 to activate the desired magnets within the heater 55 based on the settings 32.

Figure 7:
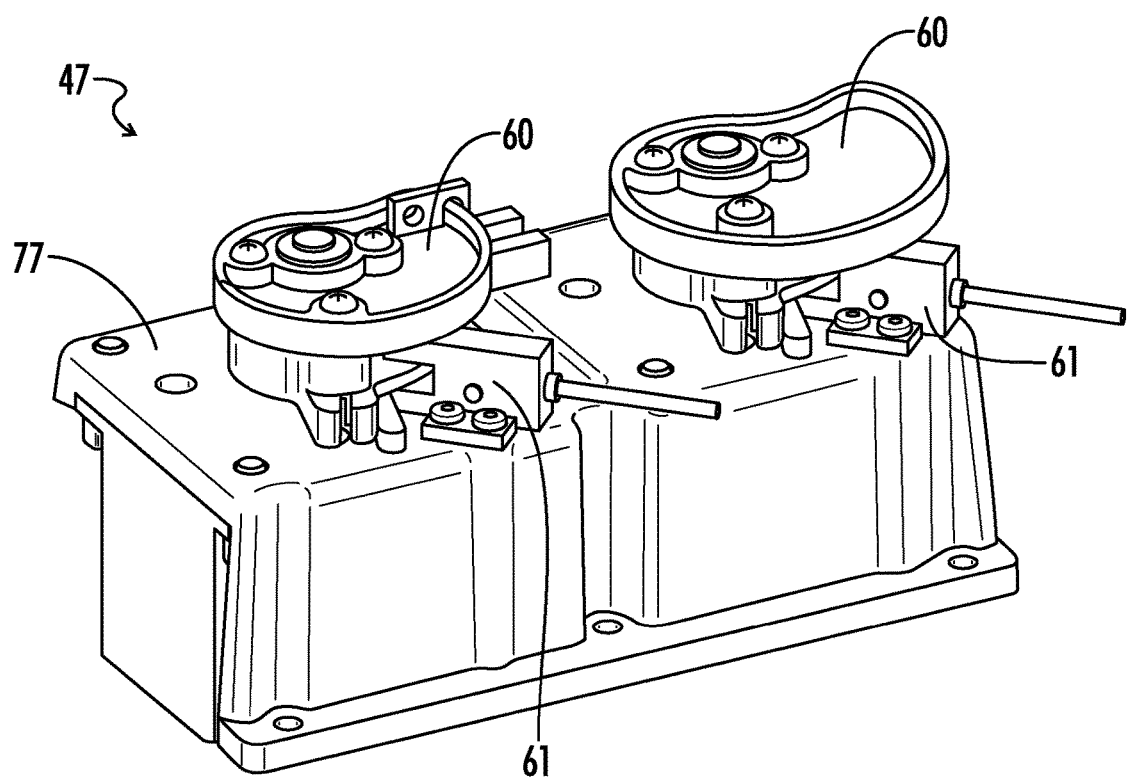
FIG. 7 is a perspective view of a lifter assembly, such as is depicted by FIG. 3.

FIG. 7 depicts an exemplary embodiment of the lifter assembly 47 of FIG. 3. As set forth above, in one embodiment, the lifter assembly 47 comprises at least one cam 60 and at least one sensor 61. The assembly 47 further comprises a base unit 77, the cams 60 and the sensors 61. The cams 60 are rotatably coupled to the base unit 77. In one embodiment, the base unit 77 contains at least one motor (not shown) for controlling rotation of the cams 60, and the base unit 77 is coupled to the onboard control element 48. The onboard control element 48 communicates with the control element 15 (FIG. 1) in order to allow the control logic 31 (FIG. 2) to control the rotation of the cams 60 based upon the predefined settings 32 (FIG. 2).

The sensors 61 are also coupled to the onboard control element 48, and the sensors 61 are configured to detect whether the corresponding cams 60 are in the home position and to transmit such detection to the control element 48. In one embodiment, the sensors 61 comprise proximity sensors, although other types of sensors 61 are possible in other embodiments. The control element 48 controls rotation of the cams 60 based upon a comparison of the detections to the desired orientation of the cams 60 as defined in the applicable settings 32. For example, if the sensor 61 detects that the cam 60 is in the home position but the heater 55 positioned above the cam 60 is required by the settings 32 to be heating the cassette 17, the control element 48 causes the motor to rotate thereby rotating the cam 60 to the engaged position, which causes the cam 60 to contact the base 56 and lift the heater 55 to the engaged position.

In one embodiment, one cam 60 is positioned beneath the cassette 17 when the cassette 17 is within the receptacle 42 (FIG. 3) such that the cam 60 is vertically-aligned with the sample chamber. Thus, when the cam 60 is rotated to the engaged position, the heater 55 aligned above the cam 60 will be lifted to the sample chamber such that the recess 70 (FIG. 6) will receive the sample chamber. Furthermore, in one embodiment, the other cam 60 is positioned beneath the cassette 17 such that the cam 60 is vertically-aligned with the detection chamber and the heater 55 aligned above the cam 60 will contact the microarray when the cam 60 is rotated to the engaged position. However, other orientations of the cams 60 are possible in other embodiments.

Figure 8:
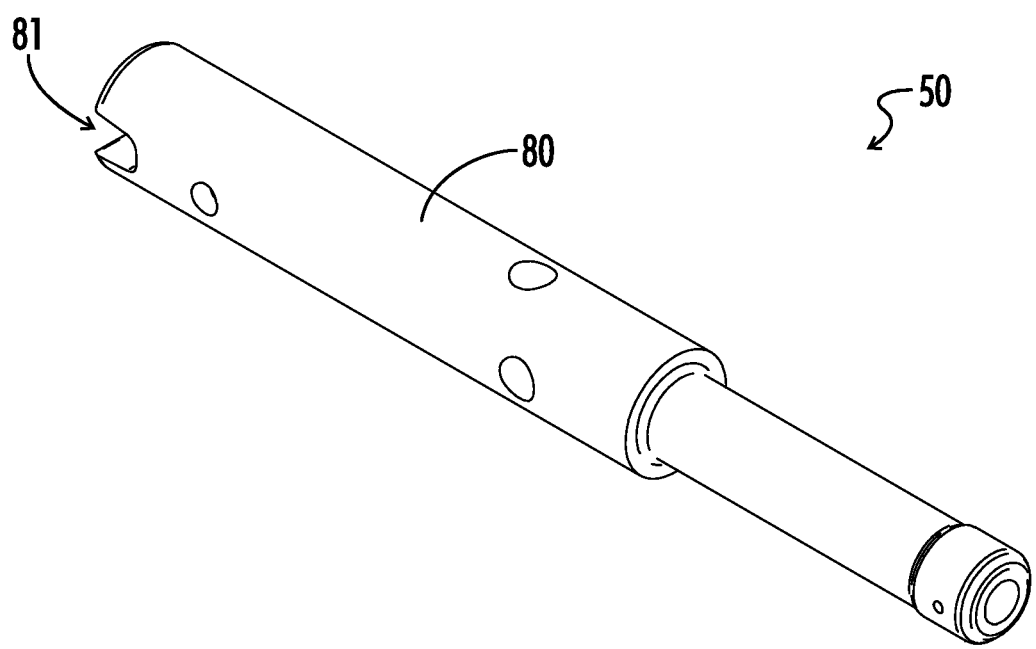
FIG. 8 is a perspective view of an exemplary cam bar shaft, such as is depicted by FIG. 3.

FIG. 8 depicts an exemplary embodiment of the cam bar shaft 50 of FIG. 3. In one embodiment, the cam bar shaft 50 comprises metal, although other materials are possible. The cam bar shaft 50 comprises a shaft portion 80 having a slot 81. The shaft portion 80 extends from the pulley 65 (FIG. 4) and into the receptacle 42 (FIG. 3). The slot 81 receives a knob (not shown) located on an end of the cam bar of the cassette 17 (FIG. 1). Thus, rotation of the cam bar motor 43 causes rotation of the shaft portion 80 thereby causing rotation of the cam bar due to the engagement of the slot 81 with the cam bar. Rotation of the cam bar adjusts the vertical position of the pipette within the cassette 17, as set forth above. While the cam bar shaft 50 of FIG. 8 has a slot 81, other means for engaging with the cam bar are possible in other embodiments.

Figure 9:
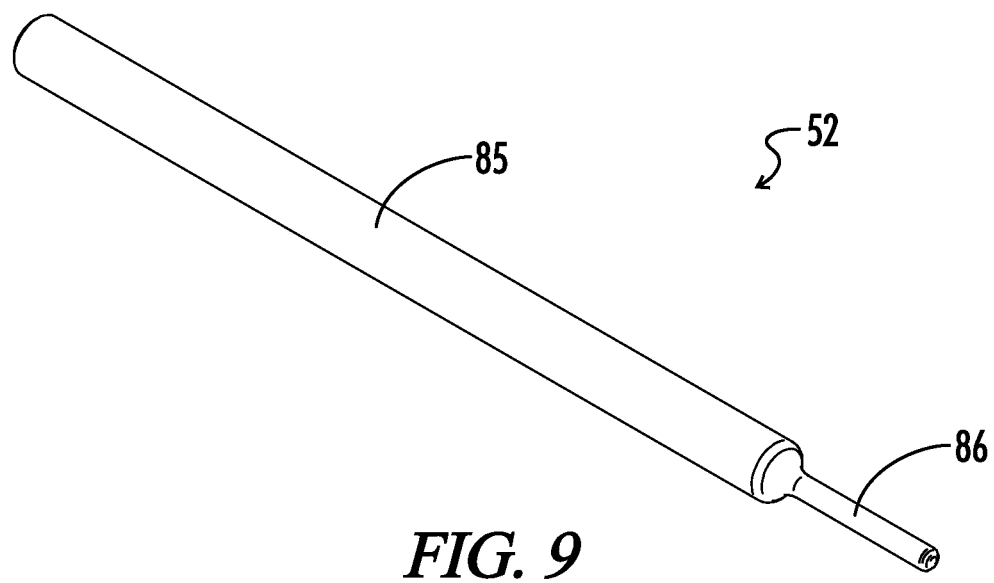
FIG. 9 is a perspective view of an exemplary plunger, such as is depicted by FIG. 3.

FIG. 9 depicts an exemplary embodiment of the plunger 52 of FIG. 3. In one embodiment, the plunger 52 comprises metal, although other types of materials are possible. The plunger 52 comprises a base portion 85 and a tip 86. The base portion 85 extends from the pump pin motor 44 (FIG. 3), and the tip 86 extends from the base portion 85 to the pump pin of the cassette 17. The pump pin motor 44 causes the plunger 52 to move in a horizontal direction thereby causing the pipette to release and expel fluids within the cassette 17, as set forth above. While the plunger 52 is disclosed in FIG. 9, other means for engaging the pump pin are possible in other embodiments.

Figure 10:
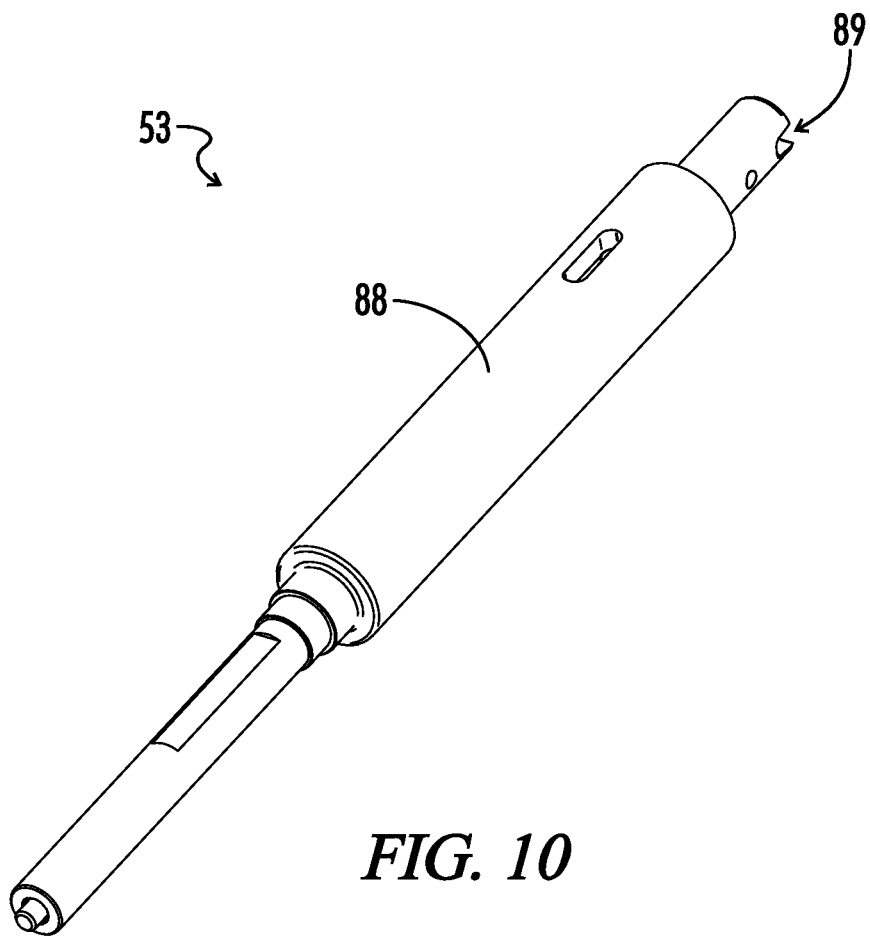
FIG. 10 is a perspective view of an exemplary lead screw shaft, such as is depicted by FIG. 3.

FIG. 10 depicts an exemplary embodiment of the lead screw shaft 53 of FIG. 3. In one embodiment, the lead screw shaft 53 comprises metal, although other materials are possible. The lead screw shaft 53 comprises a shaft portion 88 having a slot 89. The shaft portion 88 extends from the pulley (not shown in FIG. 4) coupled to the lead screw motor 45 (FIG. 3) and into the receptacle 42 (FIG. 3). The slot 89 receives a knob (not shown) located on an end of the lead screw of the cassette 17 (FIG. 1). Thus, rotation of the lead screw motor 45 causes rotation of the shaft portion 88 thereby causing rotation of the lead screw due to the engagement of the slot 89 with the lead screw. Rotation of the lead screw adjusts the horizontal position of the pipette within the cassette 17, as set forth above. While the lead screw shaft 53 of FIG. 10 has a slot 89, other means for engaging with the lead screw are possible in other embodiments.

Figure 11:
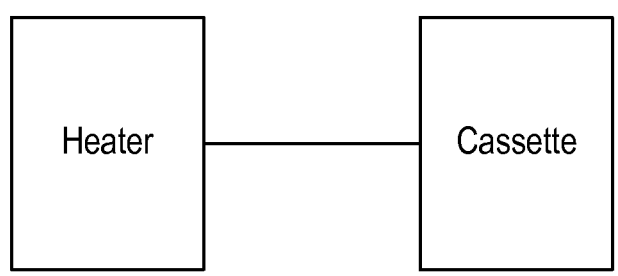
FIG. 11 depicts a heater of the heater assembly of FIG. 3 engaged with a cassette.

FIG. 11 depicts a heater 55 receiving the sample chamber of the cassette 17. The cassette 17 is positioned within the receptacle 42. As shown by FIG. 11, the lifter assembly 47 engages with the heater assembly 46. In this regard, the cam 60 of the lifter assembly 47 is rotated to the engaged position such that the cam 60 is contacting the base 56 of a heater 55. The contact between the cam 60 and the base 56 causes the base 56 to elevate with respect to the base plate 58 such that the heater 55 is lifted upward toward the receptacle 42.

The recess 70 (FIG. 6) of the heater 55 receives the sample chamber (not shown) which extends from a bottom surface of the cassette 17. The heater 55 transfers heat and/or a magnetic field to the sample chamber in order to perform steps in the arm-PCR process. The cam 60 remains in the engaged position such that the heater 55 contacts the cassette 17 until the control logic 32 (FIG. 2) instructs the cam 60 to return to the home position based upon the predefined settings 32. When the cam 60 returns to the home position, the cam 60 rotates out of contact with the base 56 such that the base 56 returns to a lowered position with respect to the base plate 58 due to gravity or a return spring (not shown).

Figure 12:
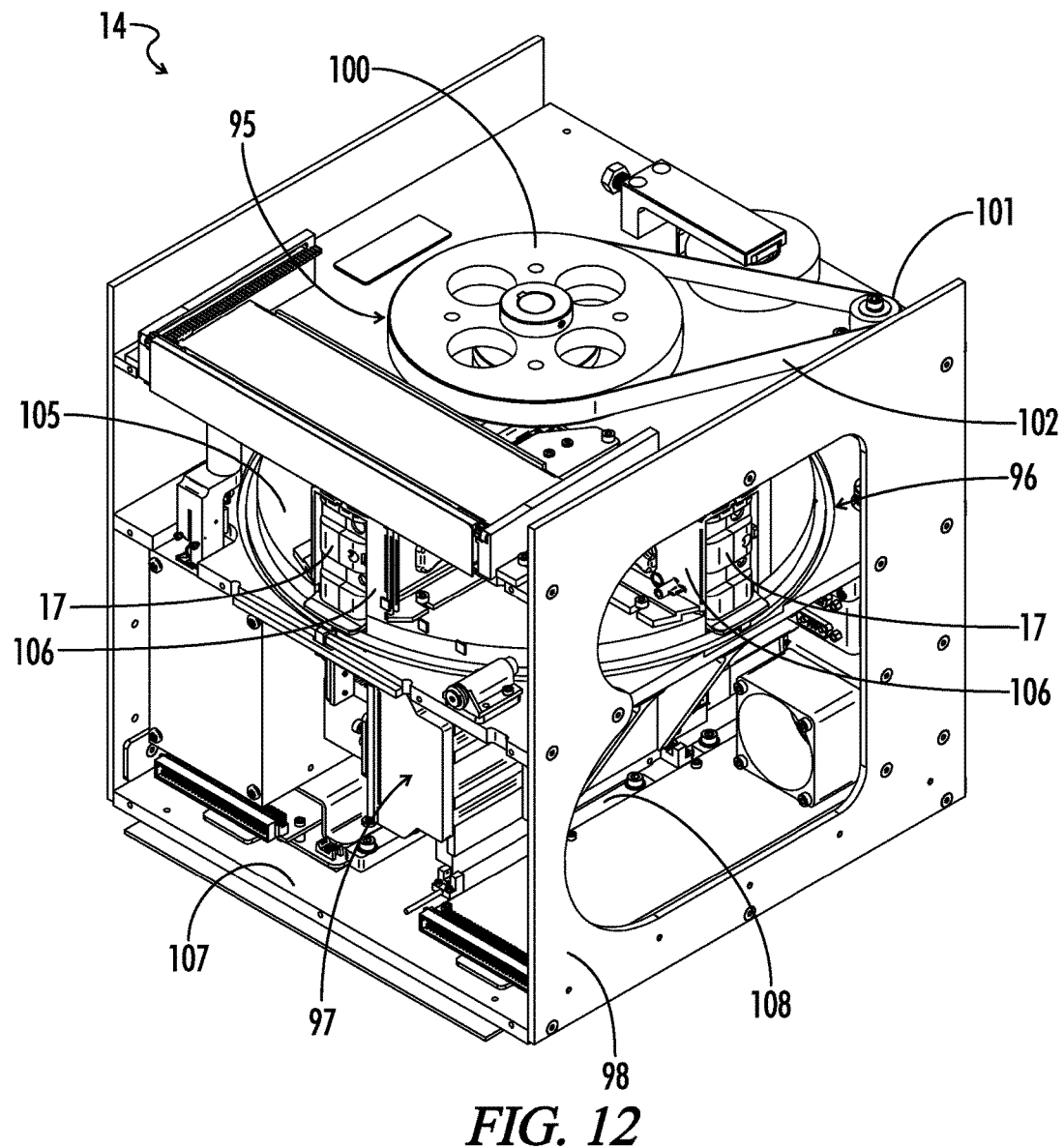
FIG. 12 is a perspective view of an exemplary embodiment of a reader, such as is depicted by FIG. 1.

FIG. 12 depicts an exemplary embodiment of the reader 14 of FIG. 1. In one embodiment, the reader 14 comprises a drive assembly 95, a flywheel assembly 96, and an optics assembly 97 positioned within a housing 98. The drive assembly 95 is positioned above the flywheel assembly 96, and the drive assembly 95 is configured to engage with the flywheel assembly 96 and control rotation of the flywheel assembly 96, as will be discussed in more detail hereafter. The drive assembly 95 comprises a large sheave 100, a small sheave 101, and a belt 102. The belt 102 fits tightly around the large sheave 100 and the small sheave 101 such that rotation of the small sheave 101 causes rotation of the large sheave 100 due to the belt 102. The small sheave 101 is coupled to a motor (not shown) via a polyflex shaft (not shown in FIG. 12) extending downwardly from the drive assembly 95, and the motor controls rotation of the small sheave 102. The large sheave 102 is coupled to the flywheel assembly 96 via a flywheel shaft (not shown in FIG. 12). Therefore, the motor controls rotation of the flywheel assembly 96 via the drive assembly 95.

The flywheel assembly 96 comprises a flywheel 105 and a plurality of receptacles 106 positioned upon a top surface of the flywheel 105. In one embodiment, the flywheel 105 is circular and has four receptacles 106 positioned upon the flywheel 105, but other numbers of receptacles and shapes of the flywheel 105 are possible in other embodiments. Each receptacle 106 is dimensioned to receive a cassette 17 (FIG. 1). Furthermore, each receptacle 106 faces an edge of the flywheel 105 such that the cassette 17 may be inserted into each receptacle 106 when such receptacle is oriented toward a front of the reader 14. The flywheel 105 has a plurality of openings (not shown in FIG. 12) for allowing the optics assembly 97 to detect a microarray of each cassette 17 positioned within the flywheel assembly 96, as will be discussed in more detail hereafter. The flywheel assembly 96 is configured to rotate at a high speed in order to allow the optics assembly 97 to quickly scan the microarray of each cassette 17 within the assembly 96.

The optics assembly 97 is slideably mounted to a flywheel support plate 110 of the housing 98. The optics assembly 97 is configured to detect the microarray of each cassette 17 positioned within the flywheel assembly 96 and to transmit data indicative of the microarray to a local control element 109. The control element 109 communicates with the control element 15 (FIG. 1) in order to control the operation of the components of the reader 14. The optics assembly 97 slides slowly along a track 108 positioned on the support plate 110 of the housing 98 such that the assembly 97 scans the entire microarray of each cassette 17 within the rotating flywheel assembly 96, as will be discussed in more detail hereafter.

Figure 13:
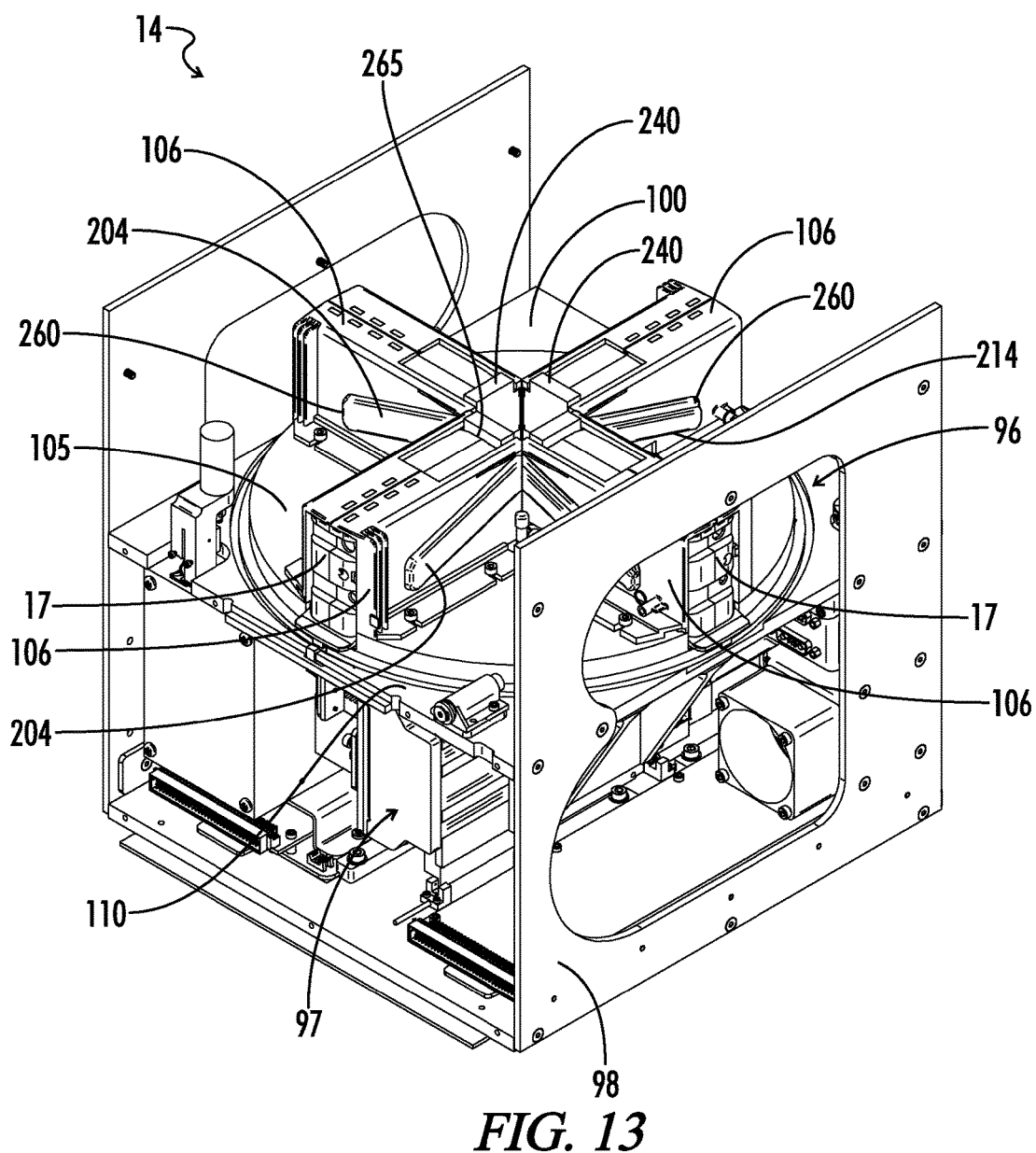
FIG. 13 is a perspective view of the reader of FIG. 12 with the drive assembly removed.

FIG. 13 depicts the reader 14 of FIG. 12 with the drive assembly 95 removed. As shown in FIG. 13, the flywheel assembly 96 comprises the flywheel 105 and a plurality of receptacles 106 positioned upon the flywheel 105. Each receptacle 106 receives a cassette 17. The flywheel 105 is positioned upon the flywheel support plate 110 rigidly mounted to the housing 98. The flywheel 105 is rotatably mounted to the support plate 110 and rotates 360 degrees with respect to the support plate 110. The support plate 110 has an opening (not shown) for allowing light from the optics assembly 97 to pass through to the microarray of the cassette 17 in order to allow the optics assembly 97 to capture data indicative of target agents detected by the microarray.

Figure 14:
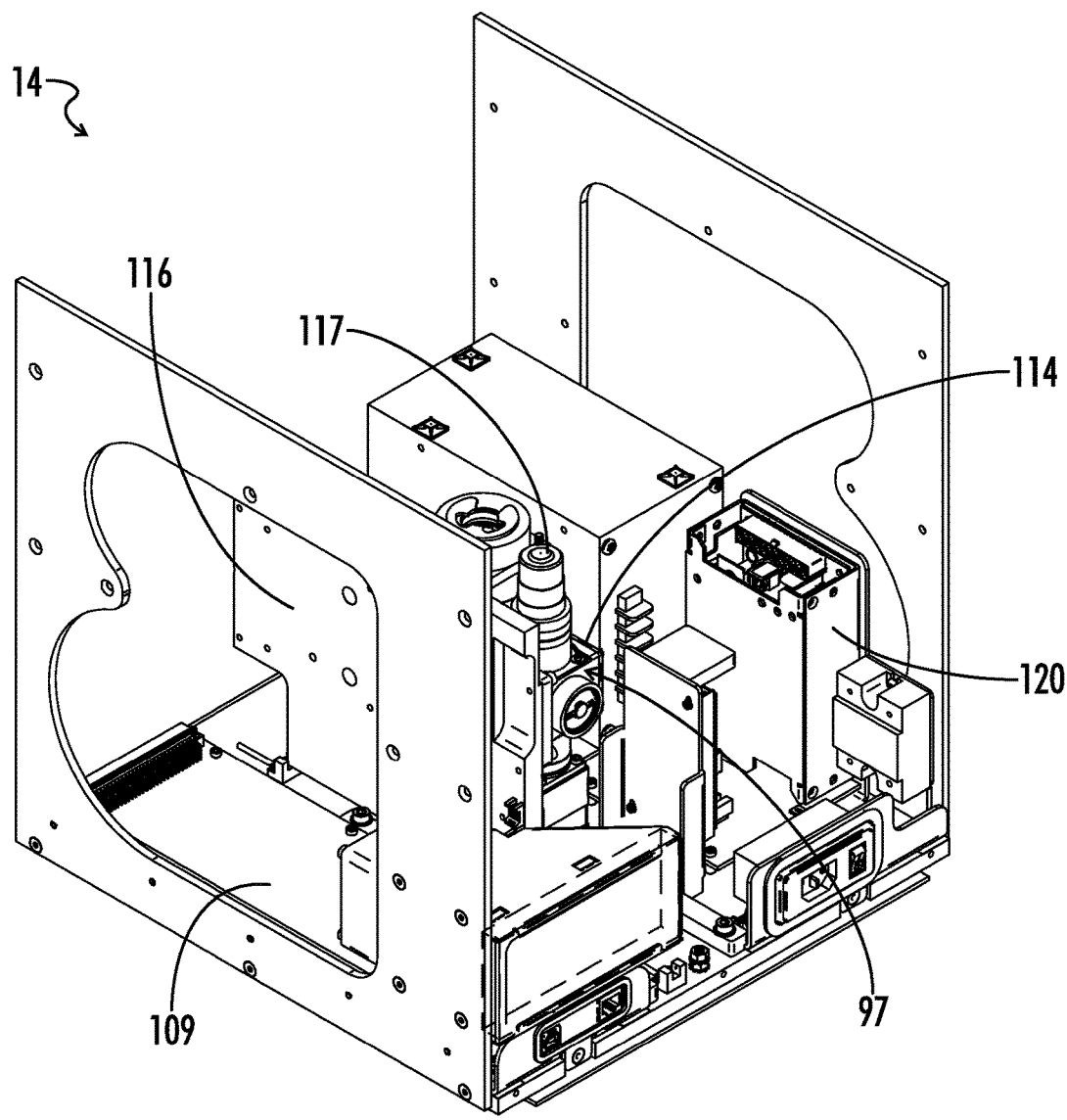
FIG. 14 is a perspective view of the reader of FIG. 12 with the drive assembly and the flywheel assembly removed.

FIG. 14 depicts the reader 14 of FIG. 12 with the drive assembly 95 and the flywheel assembly 96 removed. The optics assembly 97 comprises an optical cube assembly (OCA) 114 and a laser 115 (not shown in FIG. 14), discussed in more detail hereafter, mounted to a mounting plate 116. The OCA 114 comprises a lens 117 for detecting a microarray of each cassette 17 (FIG. 1) positioned within the flywheel assembly 96 (FIG. 12). The optics assembly 97 is coupled to the control element 109, and the optics assembly 97 is configured to transmit a signal indicative of an image of the microarray for each cassette 17 to the control element 15. The control element 15 compares the image of each cassette 17 to the predefined data 35 for the cassette 17 in order to determine whether a target agent has been detected in a specimen within the cassette 17.

The reader 14 further comprises a power supply 120 configured to supply power to components of the reader 14. The power supply 120 may supply electrical power for powering electrical components of the reader 14, such as the laser 115, the motors (not shown), and the sensors (not shown in FIG. 14).

Figure 15:
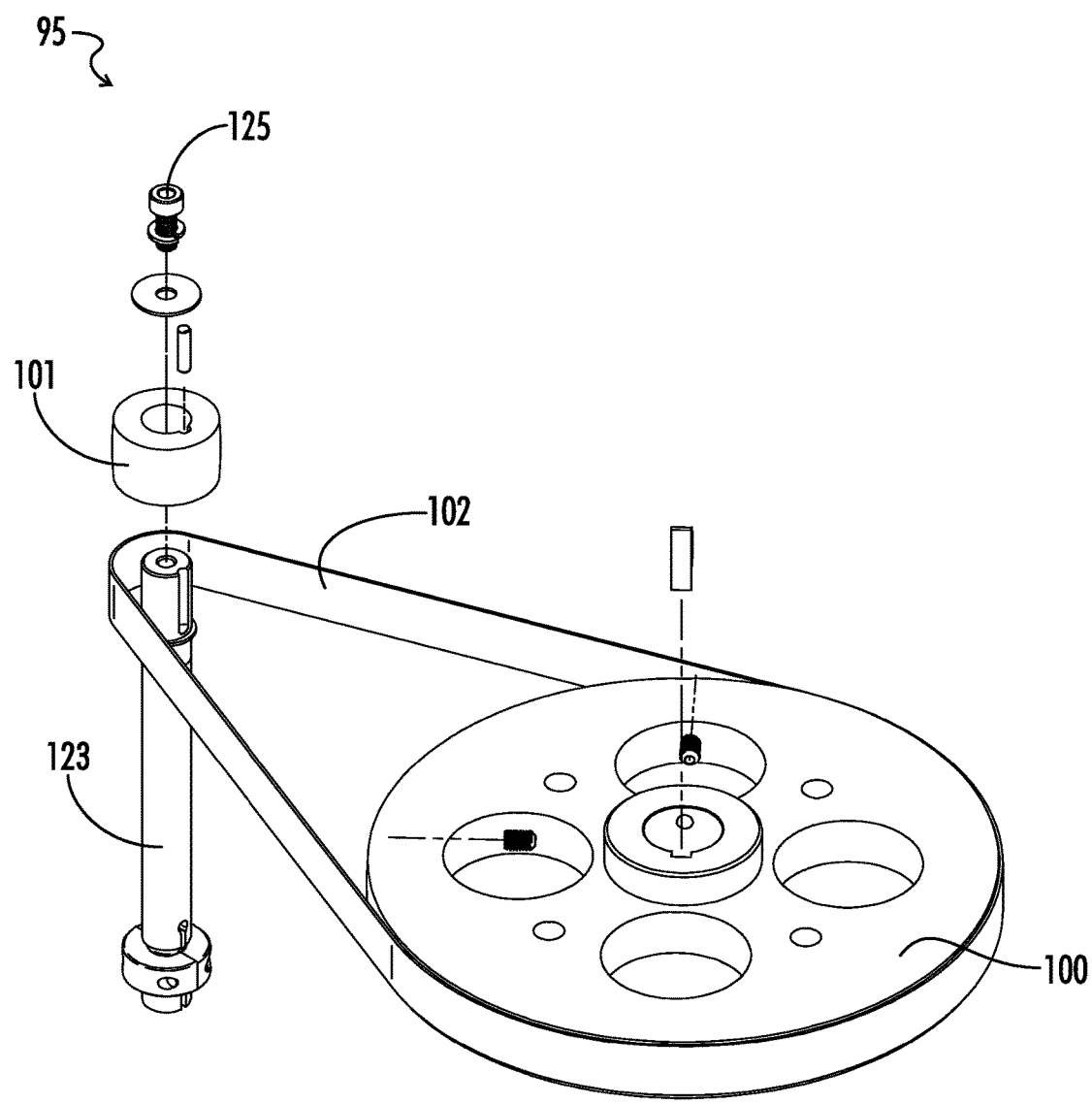
FIG. 15 is a partially exploded view of the drive assembly of FIG. 12.

FIG. 15 depicts an exemplary embodiment of the drive assembly 95 of the reader 14 of FIG. 12. As set forth above, the drive assembly 95 comprises a large sheave 100, a small sheave 101, and a belt 102. The large sheave 100 is generally circular, and the large sheave 100 is vertically aligned with the flywheel 105 (FIG. 12). The large sheave 100 is coupled to a flywheel shaft (not shown), and the flywheel shaft extends downward from a center of the large sheave 100 to a center of the flywheel 105 in order to couple the large sheave 100 to the flywheel 105.

The small sheave 101 is vertically-aligned with a motor (not shown). The small sheave 101 is coupled to a polyflex shaft 123, and the shaft 123 extends downwardly from the small sheave 101 to the motor in order to couple the small sheave 101 to the motor. The small sheave 101 is coupled to the shaft 123 via a coupling mechanism 125. In one embodiment, the coupling mechanism 125 comprises a dowel pin, a screw, a nut, and a washer wherein the screw engages with a threaded channel within the shaft in order to couple the small sheave 101 to the shaft 123. However, other types of coupling mechanisms 125 are possible in other embodiments. The motor controls rotation of the polyflex shaft 123, and rotation the polyflex shaft 123 causes rotation of the small sheave 101. The belt 102 is positioned around the large sheave 100 and the small sheave 101 such that the belt is stretched tightly and rotation of one sheave 100 and 101 results in rotation of the other sheave 100 and 101. Accordingly, rotation of the motor causes rotation of the small sheave 101, and rotation of the small sheath 101 causes rotation of the large sheave 100 via the belt 102. Rotation of the large sheave 100 causes rotation of the flywheel 105. Therefore, the motor controls rotation of the flywheel 105 via the drive assembly 95.

Figure 16:
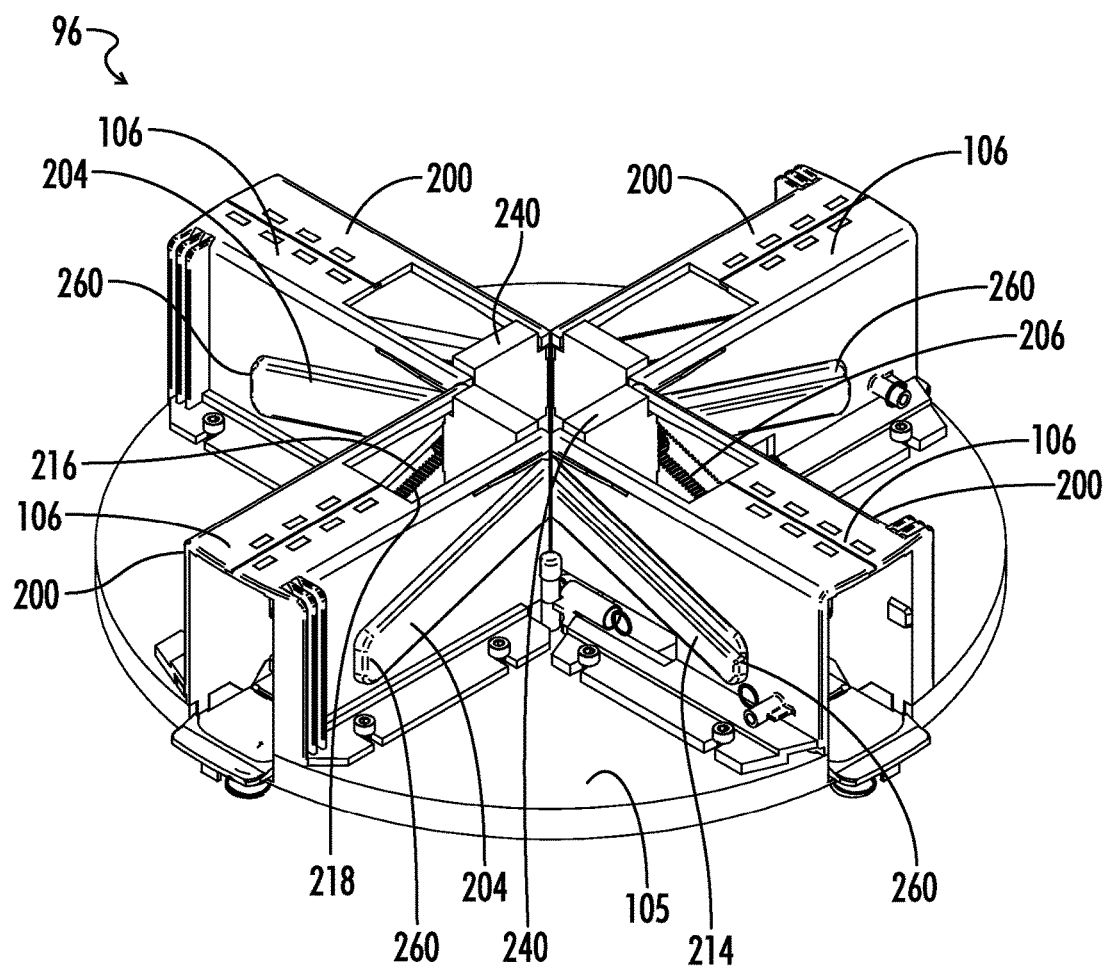
FIG. 16 is a perspective view of the flywheel assembly of FIG. 12.

FIG. 16 depicts an exemplary embodiment of the flywheel assembly 96 of FIG. 12. As set forth above, the flywheel assembly 96 comprises the flywheel 105 and a plurality of receptacles 106 positioned on a top surface of the flywheel 105. Each receptacle 106 is dimensioned to receive a cassette 17 (FIG. 1). In one embodiment, the flywheel assembly 96 comprises four receptacles 106 positioned perpendicularly to one another. Accordingly, the reader 14 may read four cassettes 17 simultaneously. Furthermore, in one embodiment, a plurality of readers 14 may be coupled to one another in order to read a plurality of cassettes 17 simultaneously. For example, twelve readers 14 may be connected in order to process forty-eight cassettes 17 simultaneously. However, other numbers of cassettes 17 may be read simultaneously by the reader 14 in other embodiments. In one embodiment, each receptacle 106 comprises an auto-balancer (not shown) for maintaining the flywheel's balance during the reading process when a cassette 17 is not positioned within each receptacle.

A flywheel shaft (not shown) extends vertically from a center of the flywheel 105 between the backs of the receptacles 106 in order to couple the flywheel 105 to the large sheath 100, as set forth above. The flywheel 105 freely rotates 360 degrees with respect to the flywheel support plate 110 (FIG. 13) in order to allow each cassette 17 to be oriented toward a front of the reader 14 (FIG. 12) as desired. Note that each receptacle 106 is positioned such that the microarray of the cassette 17 is aligned with an opening (not shown in FIG. 16) in the flywheel 105 in order to allow the optics assembly 97 to detect the microarray when the cassette 17 is positioned within the receptacle 106.

The flywheel 105 rotates at a high rate of speed, for instance at levels above 400 rpm. The flywheel 105 and other associated parts are subject to increased levels of kinetic energy during high speed rotation. As a result, the load in the flywheel 105 must be carefully balanced. Small differences in mass load can result in a large force imbalance when the flywheel 105 is rotating at high speed. Unbalanced flywheels 105 may permanently damage the reader 14 or other device components, cause injury to users of the device or cause contamination of the sample. Generally, balancing the flywheel 105 is achieved by using a combination of cassettes 17 and balance devices which all have the same weight or by using various balancing patterns without balance devices.

Figure 25:
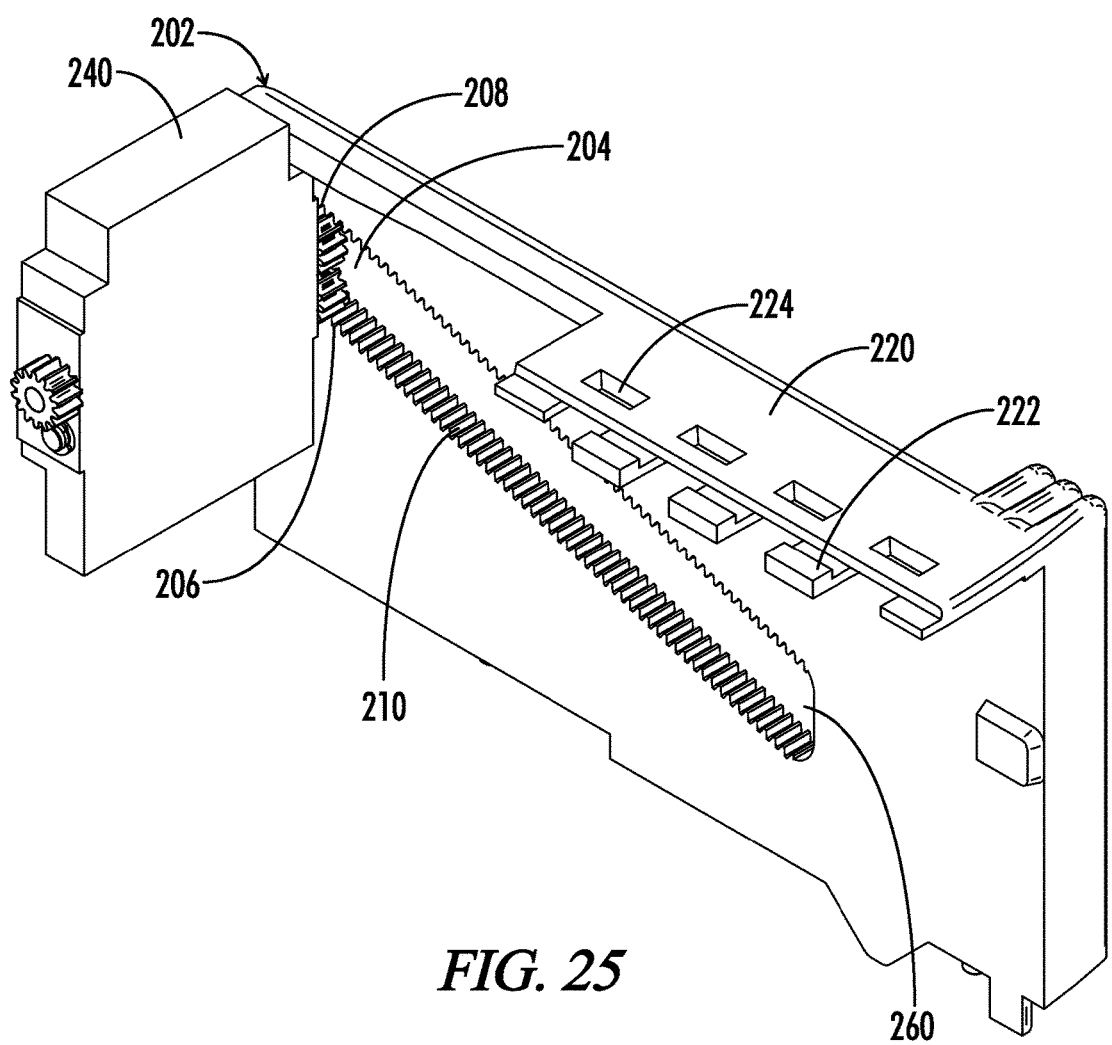
FIG. 25 is a side cut-out view of the flywheel housing comprising a balancing weight.
Figure 26:
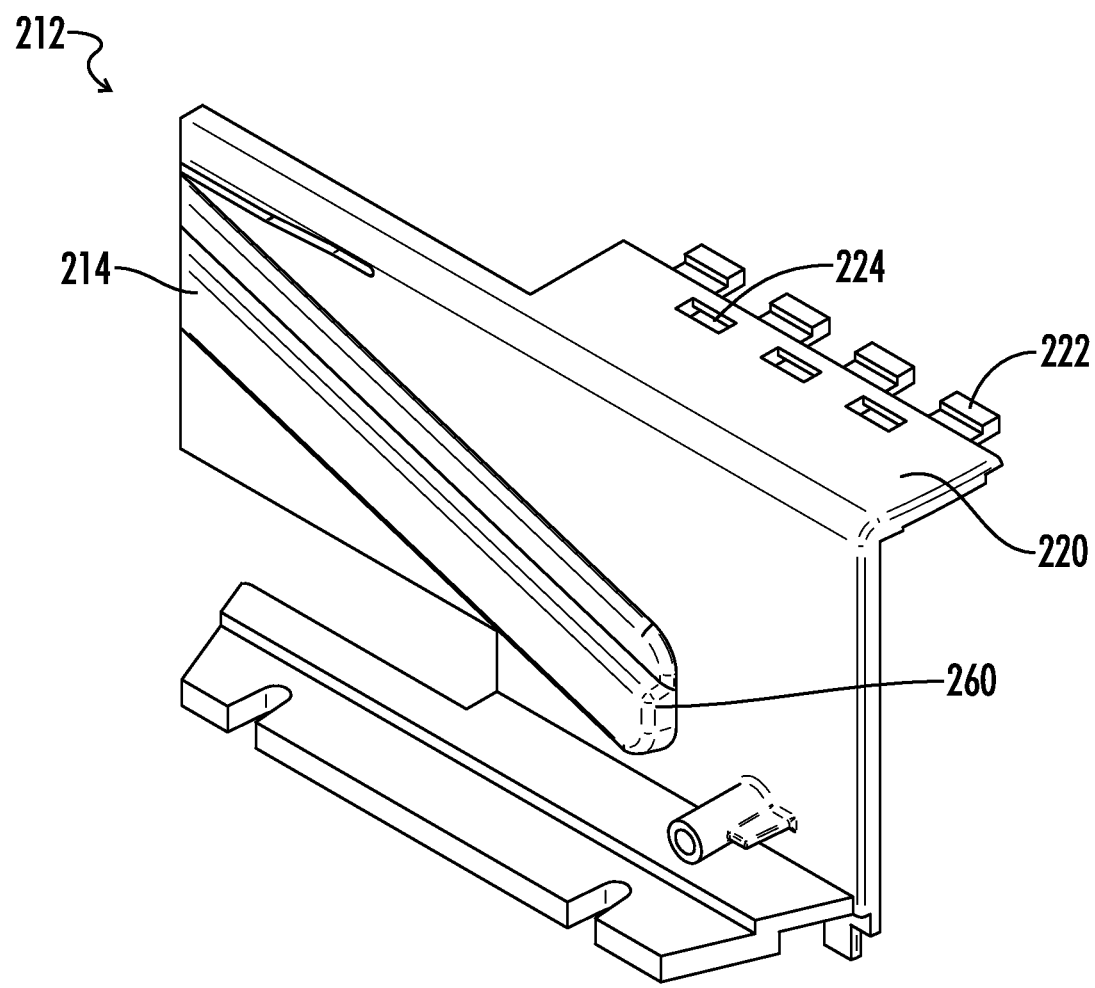
FIG. 26 is an additional side cut-out view of the flywheel housing.

FIGS. 25 and 26 depict an exemplary embodiment of the flywheel receptacle 106. In one embodiment, the receptacle 106 comprises a housing 200. Turning now to FIG. 25, the housing 200 comprises a first side 202 with an angled recess 204. The recess 204 has evenly spaced and dimensionally identical teeth 206 on the upper 208 and lower 210 sides. The teeth 206 project inwardly into the angled recess 204.

FIG. 26 illustrates a second side 212 of housing 200. The second side 212 has an angled recess 214 with evenly spaced and dimensionally identical teeth 216 on the lower side 218 (not shown, see FIG. 16). The teeth 218 project into the angled recess (FIG. 16). The first side 202 and second side 212 contain locking tabs 220 with both male pins 222 and female slots 224. Connecting the locking tabs 220 securely links the first side 202 and second side 212. When joined, the first side 202 and second side 212 form the receptacle 106 which receives the cassette 17.

Figure 27A:
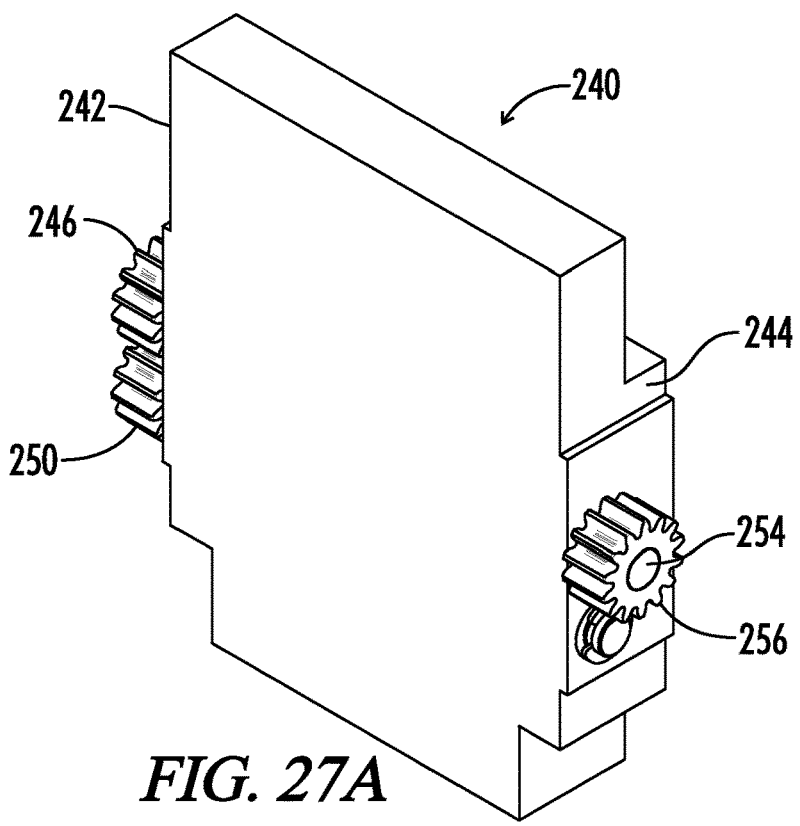
FIG. 27A is a back view of the balancing weight.
Figure 27A:
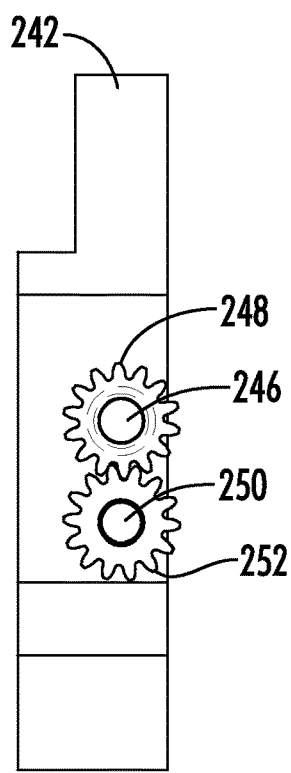
Figure 27A:
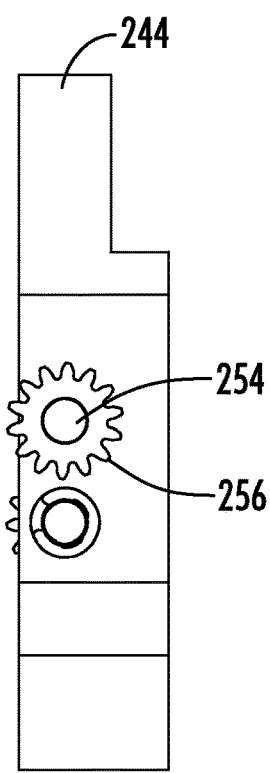

FIG. 27A depicts a geared weight 240 for use in balancing a flywheel 105 containing an uneven number of cassettes 17 during high speed rotation. The geared weight 240 comprises a first side 242 with two rotating pinion gears 246, 250. Gears 246, 250 each comprise a disk with radially projecting interlocking teeth 248, 252. The edge of each tooth 248, 252 is straight and aligned parallel to the axis of rotation. Gears 246 and 250 are precisely sized to allow their mounting into the angled recess 204 on the first side 202 of the housing 200 (FIG. 25). Here, the gear teeth 248, 252 engage with non-rotating teeth 206 (FIG. 16). Referring to FIGS. 27A and 27C, weight 240 also comprises a second side 244 with one rotating pinion gear 254 with teeth 256. Gear 254 is precisely sized to fit into angled recess 214 on the second side 212 of housing 202. Teeth 256 engage with the non-rotating teeth 216 (FIG. 16). The precise alignment of gears 246, 250 and 254 with non-rotating teeth 206 allows movement of the weight 240 up and down the angled recesses 204 and 214. Engagement of gear teeth 248, 252 and 256 with the non-rotating teeth 206 maintains weight 240 in an upright position and prevents the weight 240 from tipping, spinning or otherwise becoming misaligned within angled recesses 204 and 214.

FIG. 13 depicts an exemplary embodiment of the flywheel receptacle 106 containing a cassette 17. In this embodiment, a cassette 17 is inserted into the receptacle 106. Intersection of the cassette 27 into the receptacle 106 brings the back end 265 of cassette 17 into contact with the weight 240. Movement of the cassette 17 into the receptacle exerts a force onto weight 240 and initiates rotation of gears 246, 250 and 254. This rotation causes the engagement and disengagement of gear teeth 248 252 and 256 with non-rotating teeth 206, resulting in the movement of weight 240 up the angled recesses 204, 214. Complete insertion of the 17 cassette deposits weight 240 at the end of receptacle 106 opposite of where the cassette was inserted. Weight 240 is now located near the center of flywheel 106 and is prevented from moving down the receptacle by the presence of cassette 17 (FIG. 13). The weight 240 will therefore maintain this central location even during rotation of the flywheel 106 at high speeds. In addition, the center of balance of flywheel 106 will remain at or near the midpoint of the device, preventing any force imbalance during rotation.

In an additional embodiment, the cassette 17 is removed from receptacle 106. Gravitational forces cause the weight 240 to move down the angled recesses 204, 214. These forces cause rotation of gears 246, 250 and 254 and the engagement and disengagement of gear teeth 248 252 and 256 with non-rotating teeth 206. Weight 240 moves down angled recesses 204, 214 until gears 246, 250 and 254 rest against the bottom edge 260 of angled recesses 204 and 214. Bottom edge 260 then prevents further movement of the weight 240. As described above, engagement of gear teeth 248, 252 and 256 with the non-rotating teeth 206 maintains weight 240 in an upright position and prevents the weight 240 from tipping, spinning or otherwise becoming misaligned within angled recesses 204 and 214. After rotation begins, centrifugal forces further push the weight 240 away from the center of rotation of the flywheel 17. However, bottom edge 260 prevents weight 240 from dislodging from the flywheel 17. The placement of weight 240 near the opening of receptacle 106 creates a center of gravity similar to that observed with the insertion of a cassette 17. The flywheel 106 is therefore automatically balanced regardless of which of the housings 200 have cassettes inserted into them.

In this regard, if cassettes 17 are inserted into each housing 200, then the moments exerted on the flywheel 105 by the housings 200, including the cassettes 17 and the weights 240 (which are all pushed close to the center of the flywheel 105 as described above), are evenly distributed such that the flywheel 105 is balanced, and the flywheel should smoothly rotate without wobbling or other perturbations. If a cassette 17 is removed from any housing 200, then the weight 240 for such housing 200 automatically moves from near the center of the flywheel 105 to a position further from such center until the gears 246, 250 and 254 rest against the bottom edge 260 of angled recesses 204, 214, as described above. The mass of the weight 240 is selected so that the moment exerted on the flywheel 240 by such housing 200, which is missing a cassette 17, is substantially equal to the moment exerted on the flywheel 240 by another housing 200 into which a cassette 17 is inserted. That is, moving a weight 240 further from the center of the flywheel increases the moment induced by the weight 240 thereby accommodating the removed cassette 17. Thus, the moments exerted by all of the housings 200 on the flywheel 105 are substantially equal and evenly distributed about the flywheel 105 so that the flywheel 105 remains balanced and does not wobble or experience other perturbations during rotation regardless of which of the housings 200 actually have cassettes 17 inserted into them.

Figure 17:
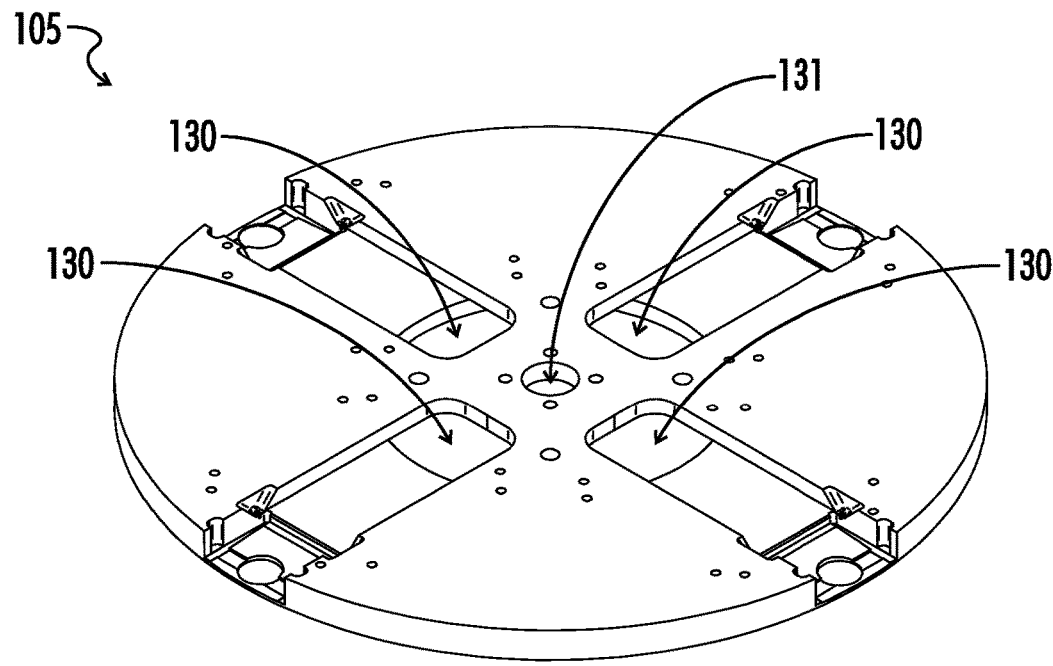
FIG. 17 is a top perspective view of the flywheel of FIG. 12.

FIG. 17 depicts the flywheel 105 of FIG. 12. The flywheel 105 has a plurality of microarray openings 130 extending vertically through the flywheel 105. A microarray of a cassette 17 may be aligned with each opening 130 in order to allow the optics assembly 97 positioned below the flywheel 105 to capture data indicative of target agents detected by the microarray of each cassette 17. In one embodiment, the flywheel 105 has four microarray openings 130 corresponding to four receptacles 106 (FIG. 12), but any number of receptacles 106 and openings 130 is possible in other embodiments.

The flywheel 105 also has a center opening 131 for receiving a flywheel shaft (not shown). The flywheel 105 is coupled to the flywheel shaft via the opening 131, and the flywheel shaft extends vertically in order to couple the flywheel 105 to the large sheave 100 (FIG. 12) of the drive assembly 95 (FIG. 12). The flywheel 105 is rotated by the drive assembly 95 via the shaft.

Figure 18:
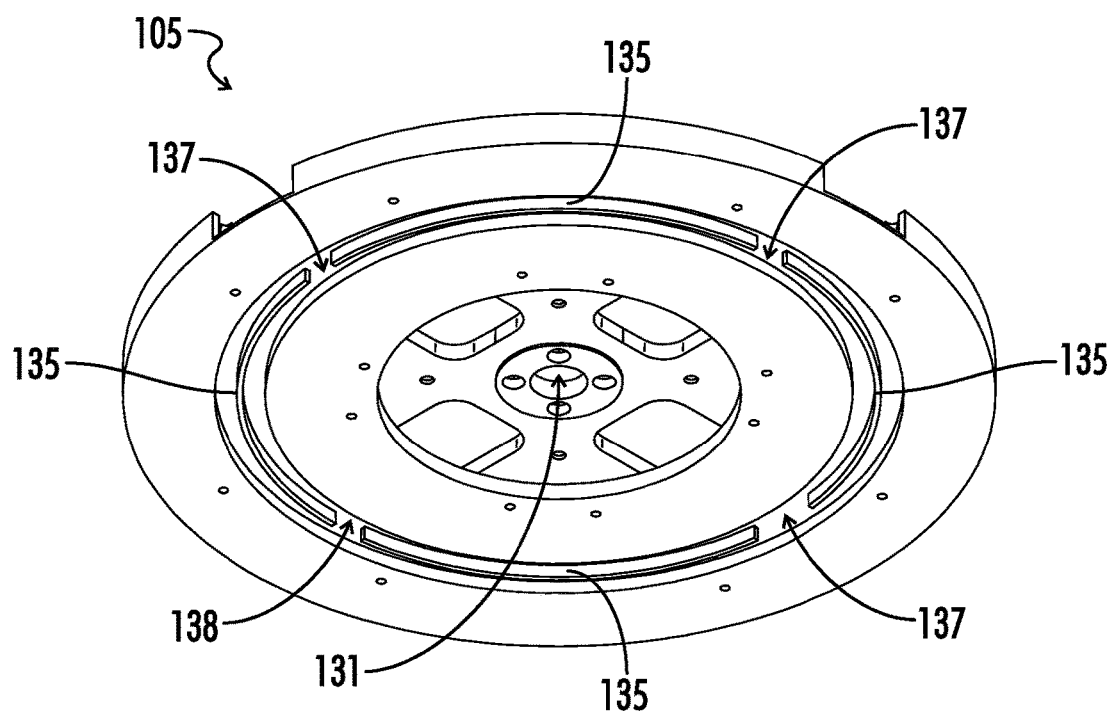
FIG. 18 is a bottom perspective view of the flywheel of FIG. 17.

FIG. 18 depicts a bottom perspective view of the flywheel 105 of FIG. 17. In one embodiment, the flywheel 105 comprises a rim 135 extending 360 degrees around the center opening 131 on a bottom surface of the flywheel 105. The rim 135 indicates the orientation of the flywheel 105 such that the control element 109 (FIG. 12) and the control element 15 (FIG. 2) may know which cassette 17 corresponds to which microarray data. As an example, in one embodiment, the rim 135 has three small gaps 137 and a large gap 138, but other numbers of gaps 137 are possible in other embodiments.

A sensor (not shown) is coupled to the control element 109 and detects the gaps 137 and 138 in the rim 135. In one embodiment, the sensor comprises a proximity sensor that detects the rim 135, although other types of sensors are possible in other embodiments. When the sensor detects a gap 137 or 138 in the rim, the sensor transmits a signal to the control element 109 indicative of the size of the gap 137 or 138. As the flywheel 105 spins rapidly, the sensor repeatedly transmits signals to the control element 109 indicating the sizes of the gaps 137 and 138 in the rim 135 thereby indicating the orientation of each cassette 17 on the flywheel 105. In this regard, the control element 109 identifies each cassette 17 by its relation to the large gap 138. The control element 109 associates each cassette 17 with its respective receptacle 106 via a detection element (not shown) that detects an identifier of the cassette 17 in the receptacle 106, or through manual input of the identifier by a user via the user input interface 26 (FIG. 2). For example, in one embodiment, the large gap 138 is vertically-aligned with a particular receptacle 106. The control element 109 associates the large gap 138 with the cassette 17 in such receptacle 106, and the control element 109 identifies such cassette 17 as the first cassette 17 and identifies all of the other cassettes 17 on the flywheel 105 by their distance in the sequence from the first cassette 17. Thus, when the control element 109 receives a signal from the sensor indicating the large gap 138 is detected, the control element 109 associates the microarray data detected by the optics assembly 97 at such time with the first cassette 17. The control element 109 further associates subsequent microarray data corresponding to the small gaps 137 with its respective cassette 17. Accordingly, the control element 109 may accurately associate microarray data with the appropriate cassette 17 based on the cassette's location with respect to the large gap 138.

Figure 19:
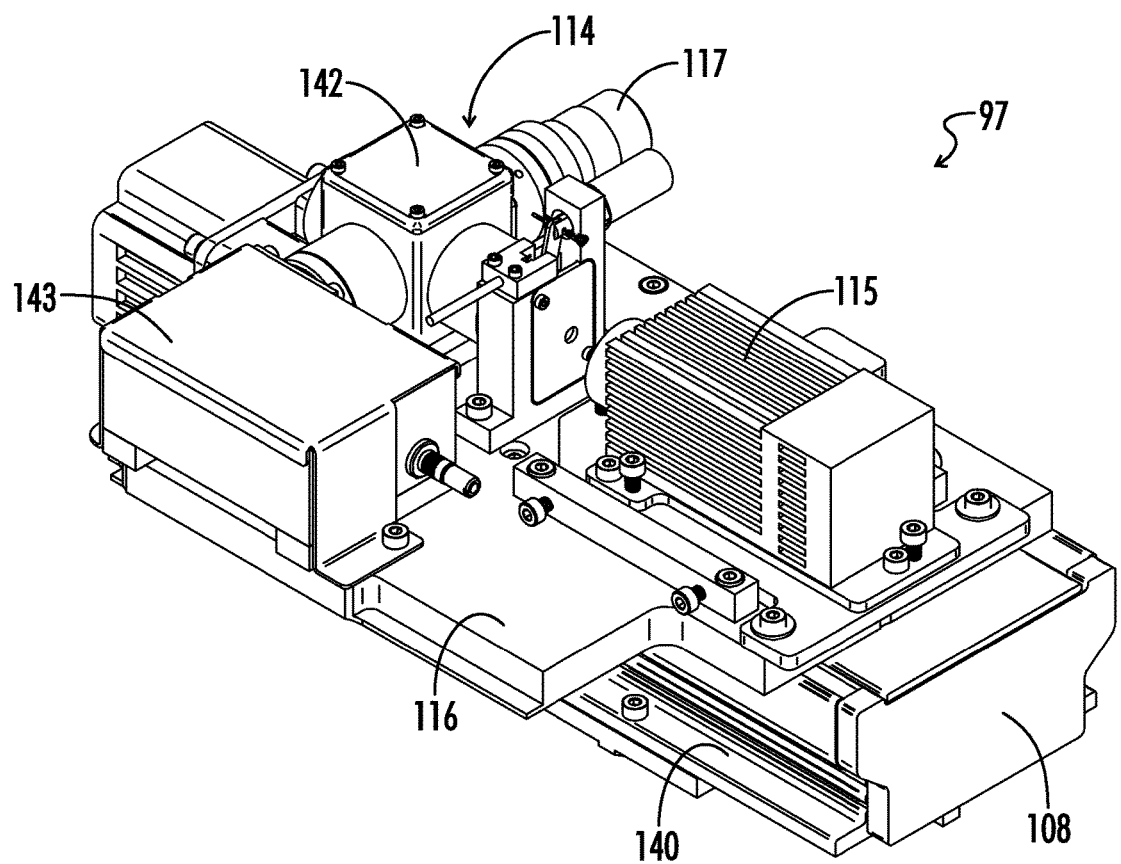
FIG. 19 is a perspective view of the optics assembly of FIG. 12.
Figure 20:
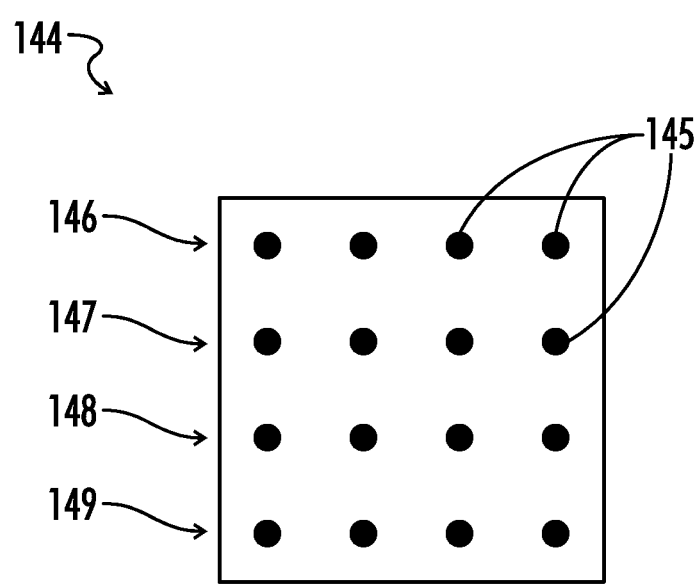
FIG. 20 is top plan view of an exemplary embodiment of a microarray.

FIG. 19 depicts an exemplary embodiment of the optics assembly 97 of FIG. 12. The optics assembly 97 comprises an OCA 114 and a laser 115 mounted to a mounting plate 116. The assembly 97 is slideably mounted to the track 108 (FIG. 12) via a rail 140. FIG. 20 depicts an exemplary microarray 144 of a cassette 17 (FIG. 1). The microarray 144 comprises a plurality of dots 145 oriented in a plurality of rows 146-149. The dots 145 are pre-formed on the microarray 144, and each dot is composed of a different material. The DNA of particular target agents bond to certain dots 145 if the target agents are present in the specimen. The exemplary microarray 144 shown in FIG. 20 comprises four rows 146-149 having four dots 145 each, but different numbers of rows 146-149, dots 145, and dot patterns are possible in other embodiments. Movement of the optics assembly 97 along the track 108 allows the optics assembly 97 to detect one dimension of the microarray 144, while rotation of the flywheel 105 (FIG. 12) allows the optics assembly 97 to detect another dimension of the microarray 144. In this regard, the optics assembly 97 performs a raster scan wherein the optics assembly 97 is stationary and scans a row 146 of dots 145 in the microarray 144 with a laser as the flywheel 105 rotates. After at least one full rotation of the flywheel 105, the optics assembly 97 slides horizontally in order to scan the next row 147 of dots 145. The optics assembly 97 continues such process until every row 146-149 of the dots 145 has been scanned. Accordingly, simultaneously rotating the flywheel 105 and sliding the optics assembly 97 along the track 108 allows the optics assembly 97 to capture data indicative of the microarray 144 on each cassette 17 positioned upon the flywheel 105.

Referring again to FIG. 19, the OCA 114 comprises a lens 117 attached to a beam splitter cube 142, and the OCA 114 is configured to determine which DNA has bonded to the dot, based on which dots fluoresce when illuminated by a laser beam, as described in more detail below. In this regard, the laser 115 transmits a laser beam (not shown) into the OCA 114 and the laser beam travels into the beam splitter cube 142. A portion of the beam is reflected and exits the OCA 114 via the lens 117. In one embodiment, a mirror (not shown) is positioned within the beam splitter cube 142 and redirects the laser beam out the lens 117, but other methods of reflecting the beam within the cube 142 are possible. The laser beam is transmitted to the microarray 144 on the cassette 17 and causes amplified DNA attached to the dots 145 of the microarray 144 to fluoresce. Fluorescent dots 145 correspond to target agents the arm-PCR process is designed to detect. In this regard, the arm-PCR process amplifies DNA corresponding to particular target agents. The amplified DNA for a particular target agent attaches to a particular dot 145 in the microarray 144 and causes the dot 145 to fluoresce when it is exposed to a laser beam. The fluorescent dots 145 are detected by a light detection element 143 via the lens 117. In one embodiment, the light detection element 143 comprises a photomultiplier tube (PMT), but different types of light detection elements 143 are possible in other embodiments. For example, in one embodiment, a high-sensitivity camera may be used to capture an image of the microarray on each cassette 17 within the reader 14.

As the optics assembly 97 moves along the track 108, each dot 145 in the microarray 145 is detected for fluorescence. If the light detection element 143 detects a fluorescent dot 145, the control logic 32 (FIG. 2) marks the dot 145 in the test data 34 (FIG. 2). The control logic 32 does so for each dot 145 in the microarray 144 such that all of the fluorescent dots 145 corresponding to detected target agents are marked in the test data 34. The control logic 32 compares the test data 34 indicative of the fluorescent dots 145 to the predefined data 35 (FIG. 2) and transmits results of such comparison to a user via the user output interface 28 (FIG. 2), as set forth above. Accordingly, the user may diagnose the specimen based on a comparison of the test data 34 to the predefined data 35.

Figure 21:
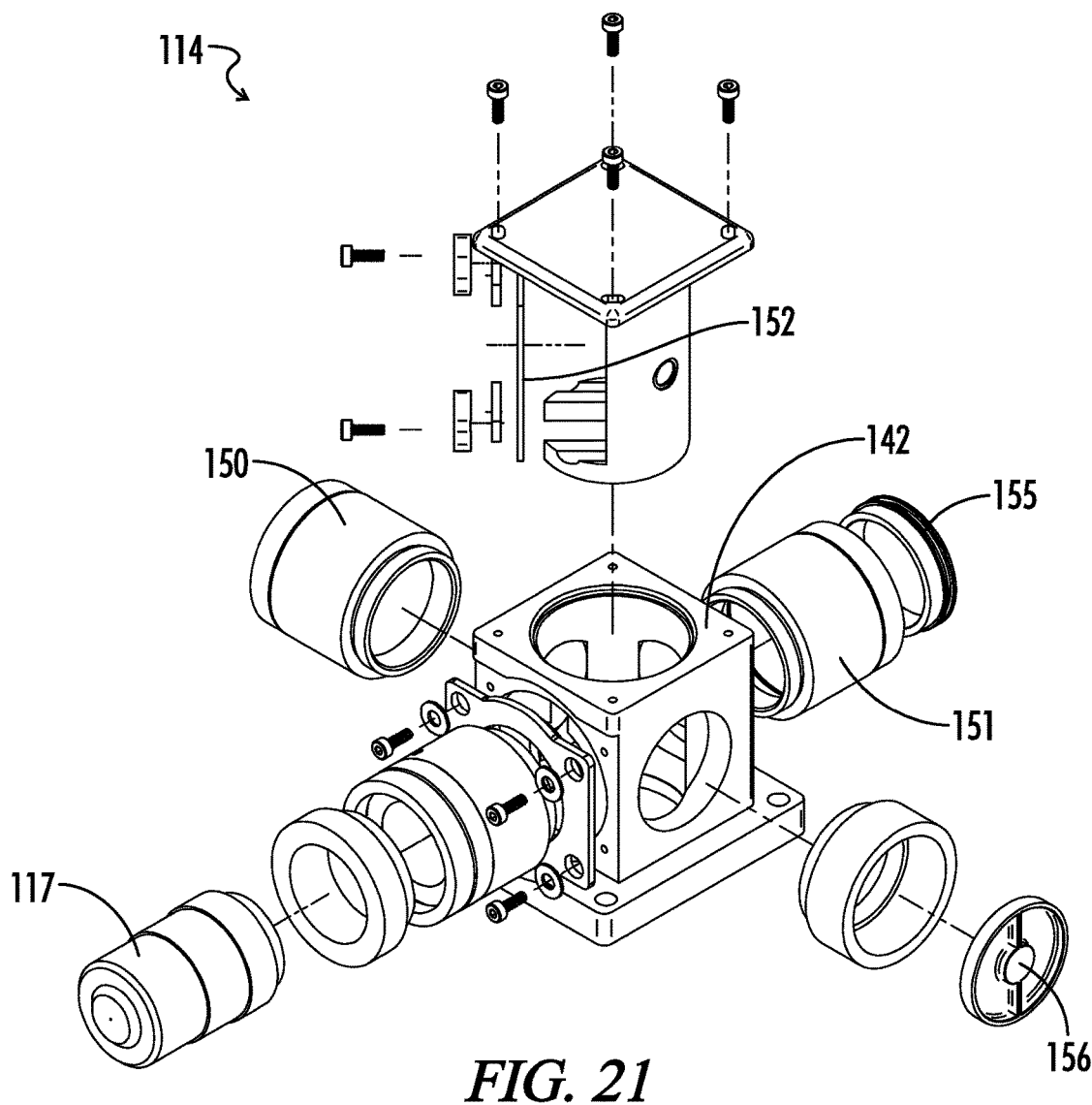
FIG. 21 is an exploded view of the optical cube assembly of FIG. 19.

FIG. 21 depicts an exploded view of the OCA 114 of FIG. 19. The OCA 114 comprises the beam splitter cube 142, the lens 117, an input member 150, and a light detection member 151. The input member 150 is positioned on a side of the OCA 114 and is oriented towards the laser 115 (FIG. 19). The input member 150 receives the laser beam from the laser 115 and allows the beam to pass into the beam splitter cube 142. A beam splitter 152 is positioned within the cube 142, and the beam splitter 152 is configured to redirect a portion of the laser beam towards the lens 117. The lens 117 is positioned on the top of the OCA 114, and the lens 117 focuses the portion of the laser beam received from the beam splitter 152 onto the microarray 144 (FIG. 20) in order to fluoresce the dots 145 of the microarray 144 to which amplified DNA is attached. Fluorescent light from the dots 145 travels back into the lens 117, through the cube 142, and out of the OCA 114 via the light detection member 151.

The light detection member 151 is positioned on the bottom of the OCA 114 and is coupled to the light detection element 143 (FIG. 19) via a sleeve 155. The light detection member 151 allows fluorescent light from the microarray 144 to pass to the light detection element 143 for transmission to the control element 109. The OCA 114 further comprises a beam dump member 156. The beam dump member 156 is configured to receive a portion of the laser beam which is not reflected through the lens 117 and to dump the laser beam. The OCA 114 redirects the laser beam from the laser 115 and captures fluorescent light from dots 145 of the microarray 144 which fluoresce due to exposure to the laser beam. Data indicative of which dots fluoresce is transmitted to the control element 15 for comparison to the predefined data 35.

Figure 22:
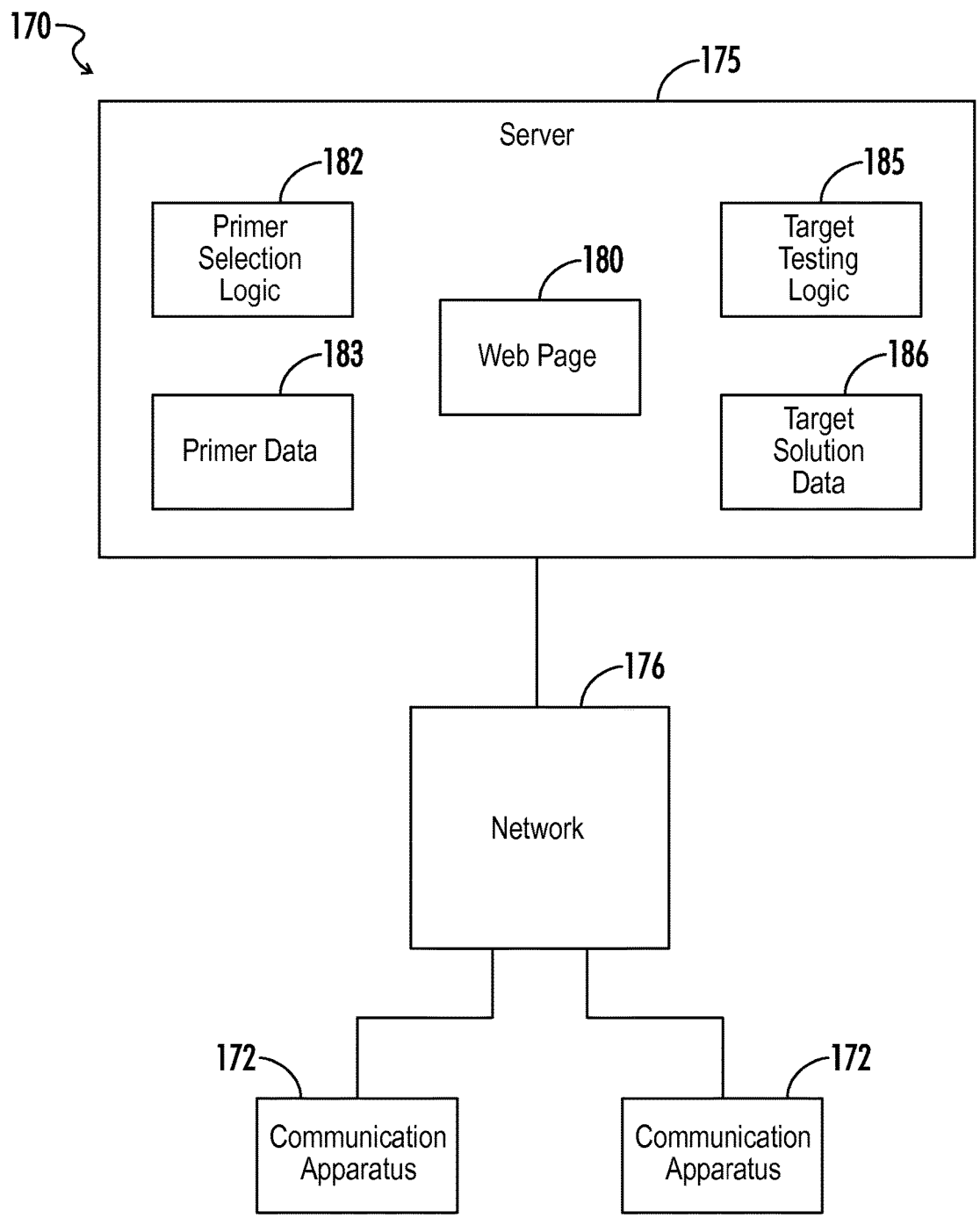
FIG. 22 is a block diagram depicting an exemplary open platform target solution system in accordance with the present disclosure.

FIG. 22 depicts an exemplary embodiment of an open platform target solution system 170. The system 170 comprises at least one communication apparatus 172 coupled to a server 175 via a network 176. In one embodiment, the server 175 hosts at least one web page 180 and comprises primer selection logic 182, primer data 183, target testing logic 185, and target solution data 186. A user, such as, for example, a target solution developer, may utilize the communication apparatus 172 to access the web page 180 in order to determine primers to use to detect a specific target agent. In this regard, the user desires to detect an unregulated target agent using the open platform system for performing PCR amplification. The communication apparatus 172 communicates with the server 175 via the network 176, such as, for example, the Internet, in order to determine the appropriate primers for a given target agent. In one embodiment, the user inputs a gene sequence for the target agent into the web page 180. Based upon the input gene sequence, the primer selection logic 182 accesses the primer data 183 and identifies at least one set of primers for detecting the target agent. In this regard, the primer data 183 correlates various primers with specific gene sequences. The primer selection logic 182 displays suggested primers to the user via the web page 180.

Based upon the suggested primers from the server 175, the user may insert such primers into the cassette 17 (FIG. 1) and perform an open platform test on a specimen by selecting a set of settings (e.g., high specificity, high sensitivity, or nominal) from the predefined settings 32 (FIG. 2), as set forth above. The user may perform as many tests as desired on the specimen using a variety of combinations of primers suggested by the primer selection logic 182 and a variety of different sets of settings 32 until a successful test is identified. In this regard, different combinations of primers and settings 32 may produce results having varying degrees of reliability in detecting the target agent. Once the user determines a test that is a reliable combination of primers and settings for detecting the target agent, the user has identified a solution for that target agent (e.g., a "target solution").

Upon determining a target solution, the user may again access the server 175 via the web page 180 in order to submit his target solution to the server 175. In this regard, the user may present his combination of primers and settings for the target agent to the server 175 as a solution for detecting the target agent, and the user may offer his combination to third party users interested in obtaining a solution for the target agent. To do this, the user accesses the server 175 via the web page 180, and the user indicates that he has determined a solution for the target agent. The user then manually inputs the target agent, the primers, and an input identifying the set of settings from the predefined settings 32 that were used in the target solution. In one embodiment, a server administrator may verify the target solution by performing the test defined by the target solution in order to ensure that the target solution is valid. However, other methods for validating the target solution are possible in other embodiments.

The target testing logic 185 provides the user with the opportunity to store the target solution in the target solution data 186. The target solution data 186 indicates primers and settings 32 for various target agents. Thus, if the user chooses to store the target solution in the target solution data 186, the target solution is available to third party users. In one embodiment, the user may offer the target solution for sale to third party users. In this regard, once the target solution is stored in the target solution data 186, a third party user (e.g., "end user") accesses the server 175 via another communication apparatus 172. The end user may then browse the target solution data 186 via the web page 180 in order to identify target solutions for a target agent he desires to detect.

Upon identifying a desirable target solution, the end user may then purchase or otherwise obtain the target solution from the server 175. In this regard, in one embodiment, the end user may provide an indication via the web page 180 that he wishes to purchase a particular target solution for a given target agent. The server administrator or the user who developed the target solution may then ship one or more cassettes 17 configured to perform the target solution to the end user. For example, such cassettes 17 may contain the proper primers for detecting the target solution and may have an identifier (e.g., a bar code) on each cassette 17, and the server administrator may update the ID mapping data 33 to map such identifier to the appropriate set of predefined settings 32 and predefined data 35 for the desired target solution. Thus, the end user receives one or more cassettes 17 configured for detecting the target solution without learning which specific primers and set of settings 32 are used in the target solution. In this regard, the system 10 may provide an indication whether the target agent is in the specimen under test without the end user realizing the details of the test. In other embodiments, the information (e.g., the primers and set of settings 32) about the target solution may be provided directly to the end user, if desired.

Figure 28:
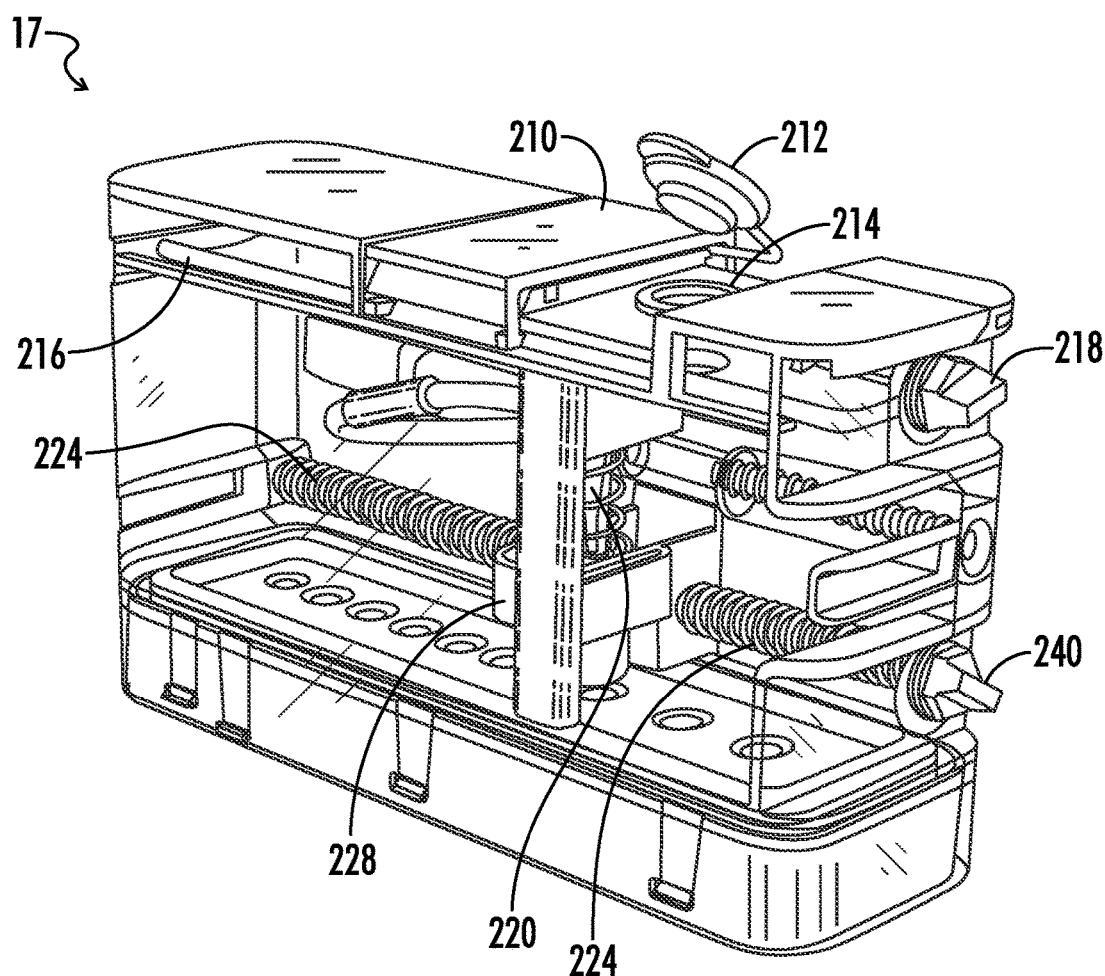
FIG. 28 depicts an exemplary embodiment of a cassette.

FIG. 28 depicts an exemplary embodiment of a cassette 17. Referring FIG. 28, the cassette has a pipette 220 that is operably connected to a rotatable cam bar 216 so that rotation of the bar 216 results in a corresponding movement of the pipette 220 upward and/or downward in a vertical direction. A pipette holder 228 supports and guides the up and down movement of the cassette pipette 220, the pipette holder 228 being supported by and slidably positioned within the cassette 17. A lead screw 224 is positioned within the cassette 17 is operably connected to the pipette holder 228 so that rotation of the lead screw 224 produces a corresponding lateral movement of the pipette holder 228, thereby forming a means for positioning the pipette 220 above the appropriate fluid well 249 at each stage of the amplification/detection process.

The base 204 of the cassette 17 comprises at least one sample chamber 242, and at least one reagent chamber 249 for containment of reagents (not shown). Reagent chamber 249 may be of identical, similar, or dissimilar size, shape, and depth and may be arranged in a variety of positions in the base 204 of the cassette 17. Desired reagents (not shown) are placed within the appropriate reagent chambers 249 so that the cassette pipette 220 may gather the reagents needed for the extraction and the two-step, two-primer-set amplification as the process proceeds within the cassette 17. Reagent chambers 249 may be pre-loaded and preferably sealed prior to shipping, with the sealing material comprising a material that will remain in place during shipping and storage but be readily punctured by the force of downward motion of the cassette pipette in order to open the reagent chamber 249 to allow retrieval of the contents using the cassette pipette 220. One such material that is appropriate for sealing the reagent chamber, either individually, or as a group, is a thin sheet of aluminum foil (not shown). In aspects of the disclosure, among the reagent chambers are two reagent chambers which will contain target-specific primers and common, non-target-specific primers, respectively. These primers are used for the first and second amplification reactions, the first amplification being target-specific to provide amplicons representing the DNA and/or RNA of the variety of targets which may be found within the sample, and the second amplification being primed by common primers to allow semi-quantitative non-specific amplification of the amplicons of the first amplification. In this two-step process, the first amplification being primed by target-specific primers provides specificity, while the second amplification being primed by common primers increases sensitivity.

Also provided in the base 204 of the cassette 17 is a detection chamber 248 containing a microarray 244 for detection of the DNA which has been amplified during the two-step ARM-PCR protocol. Microarrays are known in the art and methods for preparing target-specific microarrays are well-known to those of skill in the art.

A fill port 214 in the top of the cassette allows a user to insert a pipette (not shown) from the environment outside the cassette into a sample chamber 242. A clear plastic window (not shown) may be formed in the cassette 17 to be position so that it allows the user to see the user's pipette tip (not shown) as it is being inserted into the cassette 17 to deposit the sample (not shown) to be analyzed. In one embodiment, the clear viewing window is constructed to withstand the temperature extremes of the cassette. Alternatively, the entire enclosure of the cassette 17 may be formed from transparent or translucent plastics allowing the user to visualize the inner workings of the cassette 17.

In one embodiment, the fill port cap 212 located on top of the cassette will be a one-time operation cap, meaning that once the cap is sealed after sample insertion it cannot be reopened, thereby maintaining the integrity of the seal and keeping the system closed. In another embodiment, a sliding door 210 may be utilized such that once the sample (not shown) is introduced into the cassette 17, the sliding door 210 may be slid and locked into place. The fill port cap 212 seals the fill port 214. In one embodiment, the fill port 214 has a minimum inside diameter of 0.3 inches to allow for insertion of a 20 µl pipette through the fill port 214 and into the sample chamber 242. The fill port 214 may be other sizes in other embodiments of the present disclosure.

Movement of the cassette pipette 220 in a vertical, up-and-down manner, is provided by a cam bar 216 which is connected to a processor module 40 by means of a mechanical interface 218 immovably coupled to the cam bar 216, allowing movement of the cassette pipette 220 to be controlled by the processor module 4-. In one embodiment, the mechanical interface 18 is a knob, however, other mechanical interfaces may be used in other embodiments.

The cassette pipette 220 is supported and held in position by a pipette holder 228. The pipette holder 228 is slidably received along the length of the cassette 17. The pipette holder 228 may be retained along the same lateral plane of the cassette 17 by a first and second guiderail (not shown) which can be molded into the sides of the cassette 1. Such guiderails may be positioned vertically parallel to each other and horizontally positioned between the ends of the cassette 17. The pipette holder 228 is operably connected to the lead screw 224. The lead screw 224 is threadedly received into the pipette holder 228 by means of a male-female thread pairing between the lead screw 224 and the pipette holder 228. A mechanical interface 240 is immovably connected to the lead screw 224 allowing both clockwise and counter-clockwise rotation. Rotation of the mechanical interface 240 rotates the lead screw 224, the pipette holder 228 follows the thread of the lead screw 224 and is moved laterally along the lead screw 224 along the length of the cassette 17. Reversing the direction of rotation of the lead screw 224 causes a corresponding reversal of motion of the pipette holder 228. By controlling the number of rotations and direction of rotation of the lead screw 228, the pipette can be accurately positioned above any one of the reagent chamber 249 or sample chamber 242 located in the base 204. In one embodiment, the mechanical interface 240 is a knob, however, other types of mechanical interfaces may be used in other embodiments.

Figure 29:
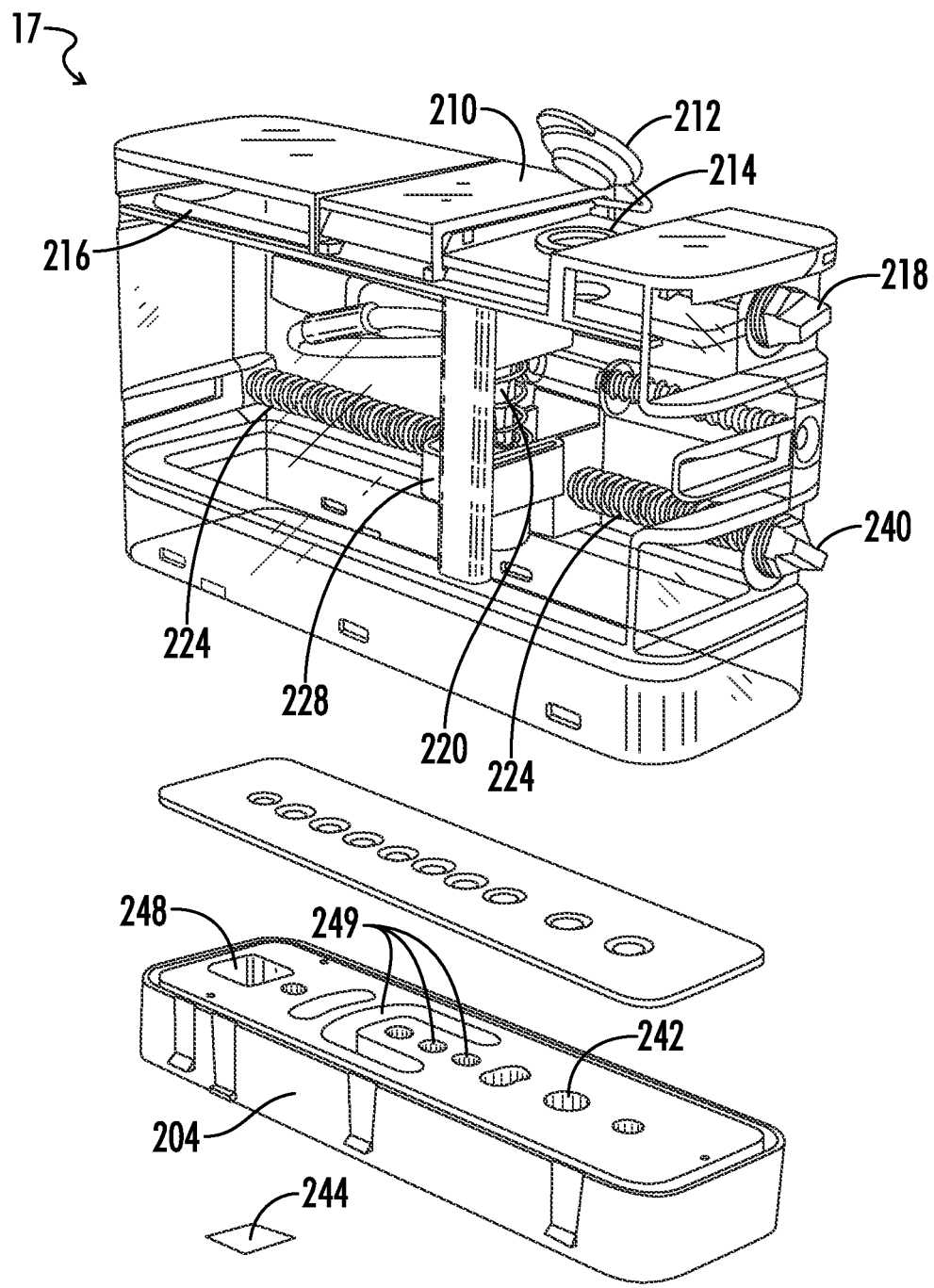
FIG. 29 depicts an exploded view of the exemplary cassette depicted by FIG. 28.

It should be emphasized that the cassette 17 of FIGS. 28 and 29 is exemplary, and other types of cassettes may be used in other embodiments.

Now, therefore, the following is claimed:

1. A system, comprising:
    a processor having a receptacle for receiving a self-contained cassette containing a nucleic acid sample, the cassette comprising a substantially closed environment surrounded on all sides by at least one barrier material thereby forming a cavity, a cassette pipette which can be moved within the cassette, and a cam bar; the processor comprising a cam bar shaft, the processor further comprising at least one heater positioned to transfer heat to the cassette when the cassette is inserted into the receptacle; and
    a control element configured to control the cam bar such that the cam bar shaft engages the cam bar and moves the pipette within the cassette, the control element further configured to control the heater for heating the nucleic acid sample to a desired temperature.

2. The system of claim 1, wherein the control element is configured to control the cam bar shaft such that the cam bar shaft rotates the cam bar for moving the pipette in a first direction within the cassette.

3. The system of claim 2, wherein the processor further comprises a lead screw shaft configured to engage a lead screw positioned in the cassette for moving the pipette in a second direction within the cassette.

4. The system of claim 3, wherein the control element is configured to control the lead screw shaft such that the lead screw shaft rotates the lead screw for moving the pipette in the second direction within the cassette.

5. The system of claim 2, wherein the processor further comprises a plunger configured to engage a pump pin positioned in the cassette.

6. The system of claim 5, wherein controller is configured to control the plunger such that the plunger moves the pump pin for drawing liquid into and out of the pipette.

7. A method, comprising:
    receiving a self-contained cassette in a processor, wherein the cassette contains a nucleic acid sample, the cassette comprising a substantially closed environment surrounded on all sides by at least one barrier material thereby forming a cavity, a cassette pipette which can be moved within the cassette, and a cam bar;
    engaging the cam bar with a cam bar shaft of the processor;
    performing polymerase chain reaction (PCR) amplification of the nucleic acid sample while the cassette is within the processor; and
    heating the nucleic acid sample via at least one heater of the processor during the PCR amplification.

8. The method of claim 7, further comprising rotating the cam bar with the cam bar shaft, thereby moving the pipette in a first direction in the cassette.

9. The method of claim 8, further comprising engaging a lead screw shaft positioned in the processor with a lead screw positioned in the cassette.

10. The method of claim 9, further comprising rotating the lead screw with the lead screw shaft, thereby moving the pipette in a second direction within the cassette.

11. The method of claim 7, further comprising engaging a plunger positioned in the processor with a pump pin positioned in the cassette.

12. The method of claim 11, further comprising moving the pump pin with the plunger, thereby moving fluid into and out of the pipette.

* * * * *